(12) United States Patent
Zamenhof

(10) Patent No.: US 12,303,310 B2
(45) Date of Patent: May 20, 2025

(54) TECHNOLOGY FOR CONTRAST-ENHANCED MAMMOGRAPHY

(71) Applicant: Robert G. Zamenhof, Brookline, MA (US)

(72) Inventor: Robert G. Zamenhof, Brookline, MA (US)

( * ) Notice: Subject to any disclaimer, the term of this patent is extended or adjusted under 35 U.S.C. 154(b) by 809 days.

(21) Appl. No.: 17/610,947

(22) PCT Filed: May 14, 2020

(86) PCT No.: PCT/US2020/032900
§ 371 (c)(1),
(2) Date: Nov. 12, 2021

(87) PCT Pub. No.: WO2020/232253
PCT Pub. Date: Nov. 19, 2020

(65) Prior Publication Data
US 2022/0249047 A1    Aug. 11, 2022

Related U.S. Application Data

(60) Provisional application No. 62/848,065, filed on May 15, 2019.

(51) Int. Cl.
*A61B 6/00* (2024.01)
*A61B 6/50* (2024.01)
(Continued)

(52) U.S. Cl.
CPC .............. *A61B 6/481* (2013.01); *A61B 6/482* (2013.01); *A61B 6/502* (2013.01); *G21K 1/10* (2013.01);
(Continued)

(58) Field of Classification Search
CPC ......... A61B 6/481; A61B 6/502; A61B 6/482; A61B 6/4476; A61B 6/035; A61B 6/547;
(Continued)

(56) References Cited

U.S. PATENT DOCUMENTS 3,778,654 A * 12/1973 Hueschen ............... C22C 27/04
378/144
4,266,133 A * 5/1981 Weigl ....................... H05G 1/32
378/115
(Continued)

FOREIGN PATENT DOCUMENTS

EP          1675152 A2    6/2006
WO    WO-2020/232253 A1   11/2020

OTHER PUBLICATIONS

Choe et al., "Optically Measured Microvascular Blood Flow Contrast of Malignant Breast Tumors," PLoS One, 9(6): e99683 (2014).
(Continued)

*Primary Examiner* — Irakli Kiknadze
(74) *Attorney, Agent, or Firm* — Dechert LLP; Andrew T. Wilkins; David M. Lee

(57) ABSTRACT

Disclosed are systems and methods for X-ray imaging of a patient's breast using optimized iodine contrast-enhanced energy-subtraction mammography (CEESM). The disclosed technology employs an X-ray tube design that uses as the X-ray target materials foils of tellurium and cerium to optimize the radiographic contrast of an iodinated contrast agent. Radiographic contrast produced by the CEESM technique is shown to be approximately 5 times higher than produced by currently existing comparable clinical techniques.

11 Claims, 18 Drawing Sheets

(51) Int. Cl.
*G21K 1/10* (2006.01)
*H01J 35/10* (2006.01)

(52) U.S. Cl.
CPC ......... *H01J 35/10* (2013.01); *H01J 2235/081* (2013.01)

(58) Field of Classification Search
CPC ..... A61B 6/4014; A61B 6/032; A61B 6/4007; A61B 6/06; A61B 6/025; A61B 6/584; H01J 35/10; H01J 35/08; H01J 2235/081; H01J 35/1017; H01J 2235/1026; H01J 2235/1093; H01J 35/1024; H01J 35/101; H01J 35/104; H01J 35/107; H01J 35/103; H01J 2235/1266; H01J 2235/1204; H01J 2235/1046; H01J 35/106; H01J 2235/085; H01J 2235/1208; H01J 2235/1086; H01J 2235/1073; H01J 2235/106; H01J 35/066; H01J 35/16; H01J 35/108; H01J 35/04; H01J 35/025; H01J 37/065; H01J 29/48; H01J 35/116; H01J 2235/20; H01J 2235/1262; H01J 2237/2482; H01J 2235/083; H01J 2235/0236; H01J 2235/086; H01J 35/02; G21K 1/10; G21K 1/02; H05G 1/025; H05G 1/66; H05G 1/52; H05G 1/46; H05G 1/12; H02P 23/20; F16C 32/064; F16C 37/002; F16C 2380/16; F16C 17/028; F16C 33/1075; F16C 17/107; F16C 33/768; F16C 35/042; F16C 43/02; F16C 23/04; F16C 23/045; F16C 17/02; F16C 17/026; F16C 33/107; H02M 1/32; H02M 7/106; F16J 15/16; B23K 26/361; G06T 11/006
USPC .......................................... 378/37, 144, 145
See application file for complete search history.

(56) References Cited

U.S. PATENT DOCUMENTS

| | | | |
|---|---|---|---|
| 4,433,431 A * | 2/1984 | Pfeiler | H01J 35/02 378/124 |
| 4,811,375 A | 3/1989 | Klostermann | |
| 4,956,859 A | 9/1990 | Lanza et al. | |
| 2001/0012329 A1 | 8/2001 | Sato | |
| 2009/0022264 A1 | 1/2009 | Zhou et al. | |
| 2010/0111260 A1 * | 5/2010 | Motz | H01J 35/28 378/143 |
| 2015/0139406 A1 | 5/2015 | Hansen et al. | |
| 2018/0333109 A1 | 11/2018 | Zamenhof | |

OTHER PUBLICATIONS

Estar: Stopping-power and range tables for electrons; National Institute of Standards and Technology, Standard Reference Database; https://physics.nist.gov/PhysRefData/Star/Text/method.html; retrieved Dec. 21, 2021.
International Preliminary Report on Patentability for International Application No. PCT/US2020/032900 dated Nov. 25, 2021.
International Search Report and Written Opinion for International Application No. PCT/US2020/032900 dated Sep. 29, 2020.
Kopans., "Digital Breast Tomosynthesis From Concept to Clinical Care," American Journal of Roentgenology, 202: 299-308 (2014).
Lewin et al., "Dual-energy contrast-enhanced digital subtraction mammography: feasibility," Radiology, 229(1):261-268 (2003).
Lewin., "Comparison of Contrast-Enhanced Mammography and Contrast-Enhanced Breast MR Imaging," Magnetic Resonance Imaging Clinics of North America: 5 pages (2018).
Madjar., "Role of Breast Ultrasound for the Detection and Differentiation of Breast Lesions," Breast Care (Basel), 5: 109-114 (2010).
Menezes et al., "Magnetic resonance imaging in breast cancer: A literature review and future perspectives," World Journal of Clinical Oncology, 5(2): 61-70 (2014).
Polemi., "Feasibility of Weighted Dual-Energy Subtraction Using Quasi-Monochromatic Beams for a Dedicated Mammotomography System," Diss. Duke University: 100 pages (2013).
Shi et al., "A multi-functional nanoplatform for efficacy tumor theranostic applications," Asian Journal of Pharmaceutical Sciences: 15 pages (2017).
U.S. Cancer Statistics Working Group. U.S. Cancer Statistics Data Visualizations Tool, based on 2020 submission (1999-2018): U.S. Department of Health and Human Services, Centers for Disease Control and Prevention and National Cancer Institute; www.cdc.gov/cancer/dataviz, released in Jun. 2021.
Werner et al., "MCNP Version 6.2 Release Notes," Los Alamos National Laboratory: 41 pages (2018).

* cited by examiner

FIG. 1

Table 2
Clinical studies comparing contrast-enhanced mammography and MR Imaging

| Study | # of Subjects | Primary Outcome | Result: CEM vs MR Imaging | Statistical Result |
|---|---|---|---|---|
| Fallenberg et al,[7] 2014 | 80 | Sensitivity[a] | 100% vs 98% | No difference |
| Jochelson et al,[8] 2013 | 52 | Sensitivity[a] | 96% vs 96% | No difference |
| Chou et al,[9] 2015 | 185 | Accuracy(AUC)[b] | 0.878 vs 0.897 | No difference |

[a] Defined as percentage of index cancers detected on each modality.
[b] AUC = area under the receiver operating characteristic curve.

FIG. 4
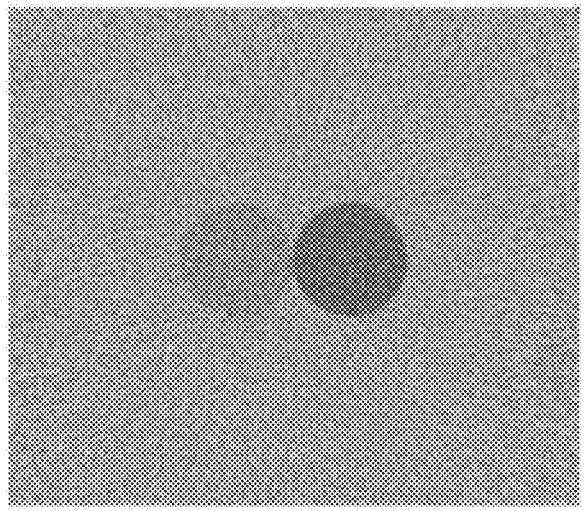
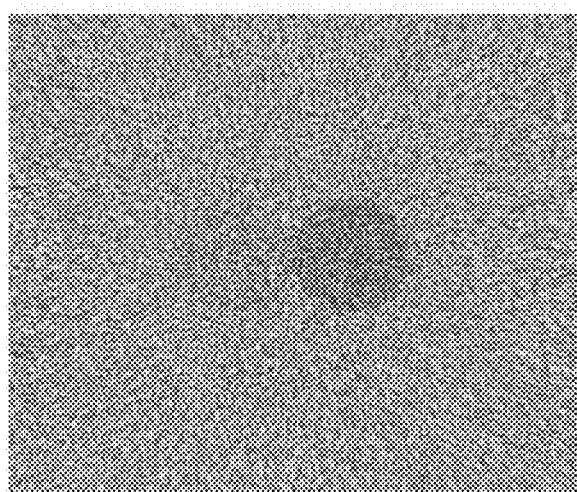
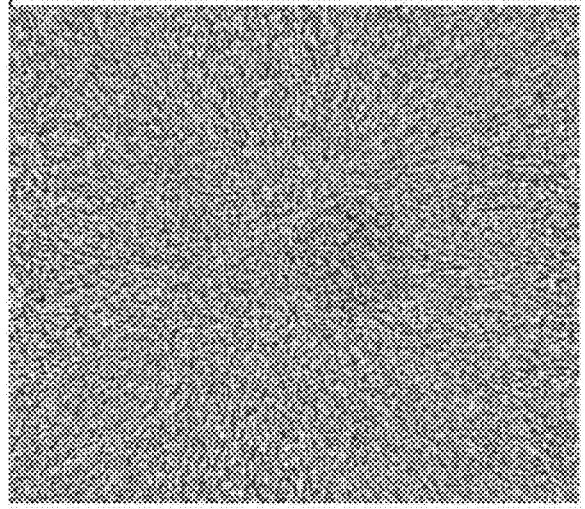

FIG. 5

| Te (keV) | Ce (keV) |
|---|---|
| 3.90* | 4.80* |
| 27.28 | 33.88 |
| 27.48 | 34.28 |
| 30.98 | 39.37 |
| 31.78 | 40.27 |
| k-Edge of Iodine: 33.16 keV | |

\* These characteristic X-rays are filtered out of the X-ray spectra of Te & Ce and do not contribute to image formation.

FIG. 6

| | Te | Ce | Mo | Rh |
|---|---|---|---|---|
| DENSITY (g/cm$^3$) | 6.24 | 6.69 | 10.28 | 12.45 |
| MELTING PT (°C) | 449.5 | 798 | 2,623 | 1,964 |
| SPECIFIC HEAT (J/kg-K) | 201 | 192 | 251 | 240 |
| DOT HAZARD CLASS | 6.1 | 4.1 | 4.1 | 4.1 |

TECHNOLOGY FOR CONTRAST-ENHANCED MAMMOGRAPHY

RELATED APPLICATIONS

This application is a U.S. National Stage Application of International Application No. PCT/US20/32900, filed May 14, 2020; which claims the benefit of priority to U.S. Provisional Patent Application No. 62/848,065, filed May 15, 2019.

BACKGROUND

Early detection and diagnosis of breast cancer is essential for maximizing the likelihood of successful treatment. In the United States breast cancer accounts for 32% of cancer incidence in women and 18% of cancer deaths (1). This translates to 40,600 female breast cancer deaths every year. Therefore, any improvement in the technology of diagnosing breast cancer would have a major impact on public health.

Currently, screening mammography (i.e., routine mammographic exams of the adult female population) is done using dedicated mammography X-ray equipment that utilizes X-ray exposure using molybdenum, rhodium, or tungsten X-ray spectra. Screening mammography is primarily intended to identify subjects who do not have breast cancer, but if a diagnosis is either ambiguous or positive, 'diagnostic' mammography is usually done as a follow-up exam, invoking additional diagnostic tools for assessing the breast, such as spot-compression or magnification X-ray mammography, breast MRI with gadolinium contrast enhancement (2), or ultrasound (3).

Another recent advance in X-ray screening mammography has been digital breast tomosynthesis (DBT) (4). In this procedure, X-ray images of the breast are obtained without contrast by acquiring 15-20 individual exposures of the breast over a 15-20 degree angular sweep of the X-ray beam, followed by reconstruction of the data into pseudo-3D parallel image planes through the breast. 'Paging' through these parallel planes aids the mammographer by displaying overlapping breast tissues as separate layers so that there is less likelihood of lesions being obscured. This technique has been shown to improve screening accuracy over conventional mammography, particularly in patients with large and/or dense breasts, and is becoming a routine procedure in screening mammography centers.

There is compelling evidence that angiogenesis factors modulate the formation of abnormal microvasculature around and within breast cancers. Therefore, the use of a contrast agent can help highlight the breast microvasculature and also potentially highlight breast tumors. Contrast-enhanced MRI (CMRI) was introduced in mammography to exploit these possibilities. Although CMRI has a high sensitivity for detecting breast cancers, it has significant disadvantages, including decreased specificity due to parallel enhancement of various benign abnormalities such as fibroadenomas, as well as high cost and long procedure times. CMRI also precludes the imaging of women with surgical metal clips or those patients who suffer from insurmountable claustrophobia.

Since 2003 much interest has been devoted to contrast-enhanced dual-energy mammography (CEDEM) (5). Currently, as is the case of CMRI, CEDEM is used exclusively when conventional screening mammography has yielded ambiguous or positive results and additional information is required about the pathologic identity of the detected abnormality. In the CEDEM procedure, an iodine-based contrast agent is introduced into the patient. Dual-energy X-ray images are taken after the contrast agent has distributed itself in the breast microvasculature. The dual-energy pairs of X-ray images are then subtracted from each other. The subtraction procedure suppresses normal breast tissue architecture, often referred to as 'clutter,' enhancing the detectability of breast tumors and other breast lesions.

Contrast-enhanced mammography has been clinically evaluated using two distinct approaches:

1) Temporal subtraction involves subtraction of images obtained at single X-ray energies pre- and post-contrast administration.
2) Dual-energy subtraction (the CEDEM technique) involves subtraction of only post-contrast administration images taken within short intervals at two different X-ray energies. In the CEDEM technique, images are obtained using low and high X-ray energy spectra, shaped to bluntly correspond to regions above and below the k-edge of iodine (at 33.16 keV). The 'shaping' process includes the use of molybdenum/rhodium dual-energy X-ray tubes and selection of kVp's and X-ray filters. Since X-ray energies above the k-edge of iodine are absorbed much more strongly than those below, subtraction of the 'low-energy' from the 'high-energy' images strongly enhances the iodine contrast while suppressing the anatomical clutter of normal breast anatomy. This, as already mentioned, increases the detectability and differentiability of breast abnormalities including breast tumors. An advantage of the dual-energy subtraction technique compared to the temporal subtraction technique is that dual-energy pairs of images are obtained with very short inter-exposure time delay. Therefore, the subtracted images are minimally degraded by breast movement or blood vessel pulsation. In the case of the temporal subtraction technique, however, there may be a delay of up to a minute separating pre- and post-contrast image acquisition, which can increase the likelihood of subtraction image degradation due to breast movement or blood vessel pulsation. Lewin (6) has summarized the diagnostic sensitivity of CEDEM vs CMRI for evaluating the breast. FIG. 1 (from Lewin) shows this comparison, where it can be seen that statistically CEDEM and CMRI have equal sensitivity for detecting breast cancer.

SUMMARY

Disclosed herein is a novel technology for breast imaging: 'optimized iodine contrast-enhanced energy-subtraction mammography' (CEESM). The presently disclosed CEESM breast imaging technology not only matches the high breast tumor detection levels of CEDEM and CMRI, but significantly exceeds them, while still maintaining relative to CMRI the advantages of reduced procedure cost, reduced procedure time, and the ability to include patients with metallic implants and those suffering from insurmountable claustrophobia.

The principle of CEESM is to exploit the k-edge of iodinated contrast agents as used in contrast-enhanced mammography and in other X-ray procedures that require contrast enhancement. Instead of utilizing molybdenum, rhodium, or tungsten to produce X-rays, the CEESM technique utilizes two X-ray target elements, tellurium (Te) and cerium (Ce), that optimize the effectiveness of energy subtraction related to the k-edge of iodine. Based on theoretical calculations, CEESM greatly exceeds the tumor detectability of non-contrast mammography (74-78%) and closely matches the improved detectability of current contrast-enhanced mammography (95-100%) and CMRI (96-98%). Relative to CMRI, this can be achieved at greatly reduced procedure cost and with no patient exclusion issues related to metallic objects in the body or to insurmountable claustrophobia. More specifically, under a range of mammographic imaging conditions, the radiographic contrast of iodine produced by the CEESM technique is about 5 times higher than that produced by the existing CEDEM technique as clinically used for contrast-enhanced mammographic imaging. Finally, the disclosed CEESM technique also has diagnostic applications beyond mammography, including contrast-enhanced fluoroscopic imaging in neuroradiology with 'on-the-fly' image subtraction at fluoroscopic image acquisition rates, as well as at other anatomical sites that are less than about 15 cm thick.

In certain aspects, the present disclosure relates to an apparatus for X-ray mammography, comprising an X-ray tube, wherein the X-ray tube comprises: an anode and a focal spot track, wherein the focal spot track comprises a tellurium foil and a cerium foil.

In some aspect the present disclosure relates to an image acquisition and X-ray generation control system, comprising:
  a first control system adapted to initiate and terminate rotation of an anode and heating of a filament;
  a second control system adapted to apply and remove a voltage of about 50,000 volts between the anode and the filament;
  an X-Ray tube comprising a focal spot track, wherein the focal spot track comprises tellurium and cerium, and wherein the X-Ray tube is adapted to produce tellurium and cerium X-ray production pulses with a start time and a stop time for each pulse;
  a monitor adapted to synchronize rotation of the anode to the start and stop times of the tellurium and cerium X-ray production pulses; and
  an image processing module adapted to:
  generate tellurium and cerium dual-energy image pairs,
  scale and subtract the tellurium and cerium dual-energy image pairs, thereby generating image data,
  store the image data, and
  transmit the image data to an image display module.

In some aspect the present disclosure relates to a method of X-ray imaging of a tissue in a subject, comprising: administering to a subject an iodine-based contrast agent; positioning the subject in the apparatus; and acquiring an image of the tissue of the subject.

BRIEF DESCRIPTION OF THE DRAWINGS

FIG. 1 shows a table comparing sensitivities of contrast-enhanced mammography (referred to by Lewin as CEM) vs. CMRI for the detection of breast cancer.

FIG. 4 shows two simulated breast 'tumors' with a contrast difference of 5. The difference between the three panels is the degree of statistical noise that has been added to the simulated tumor images.

FIG. 5 shows characteristic X-ray energies of tellurium (Te) and cerium (Ce) and the k-edge energy of iodine.

FIG. 6 shows physical properties of tellurium (Te), cerium (Ce), molybdenum (Mo), and rhodium (Rh).

DETAILED DESCRIPTION

Conventional mammography is currently performed with single-energy X-ray spectra using either rhodium (Rh), molybdenum (Mo), or tungsten (W) as the X-ray target materials. The Rh and Mo X-ray spectra are produced in so-called 'dual-energy' X-ray tubes. Such X-ray tubes were originally designed for screen-film mammography (i.e., either Mo or Rh X-rays were selected depending on the patient's breast size and composition), and are still used nowadays for contrast-enhanced dual-energy mammography in the CEDEM technique as described by Lewin (5) and implemented in the SenoBright™ Spectral Mammography system marketed by General Electric Corp. Since the advent of digital mammography in the early 2000's, single-energy X-ray tubes producing tungsten X-ray spectra filtered by a variety of materials (e.g., Al, Ag, Rh) have been more frequently used for conventional screening mammography.

CEESM, as disclosed herein, improves the breast tumor detectability from 74-78%, as reported for conventional mammography, to almost 100%, as is reported for both contrast-enhanced MRI (CMRI) and contrast-enhanced dual-energy mammography (CEDEM). This comparison is summarized in FIG. 1 from Lewin (5).

Figure 2:
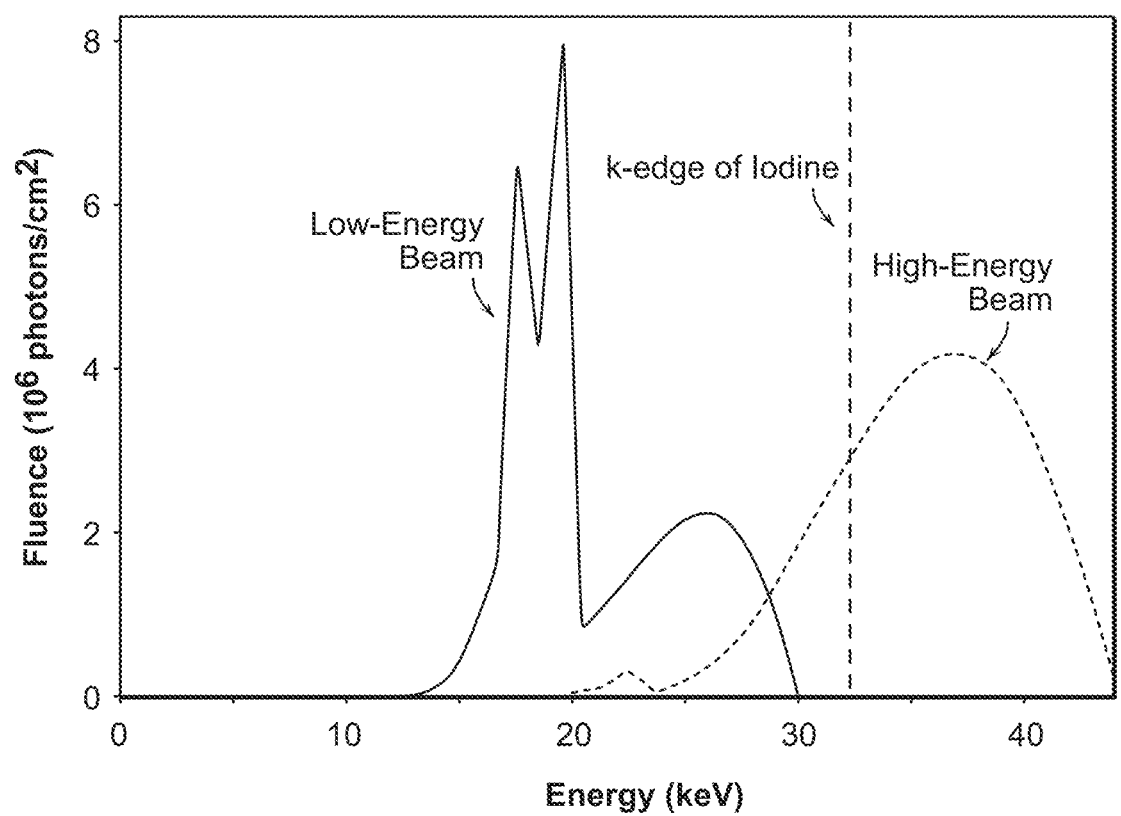
FIG. 2 shows calculated X-ray spectra from Lewin (5). 'Low energy' spectrum uses a Mo target, 30 kVp, and 0.03 mm Mo filter. 'High energy' spectrum uses a Rh target, 44 kVp, 0.025 mm Rh filter plus 8 mm Al filter. X-ray spectra are displayed with respect to the k-edge of iodine at 33.16 keV.

The question arises as to what practical benefit would a new mammography technique have if it competes with an existing technique that already have a sensitivity of almost 100%? The answer to this is suggested by a mathematical simulation shown in FIG. 2. This illustrates a comparison between two simulated 'lesions' in a breast that differ in radiographic contrast by a factor of 5, which is the approximate factor by which the radiographic contrast of the CEESM technique is higher than that of the CEDEM technique using comparable experimental parameters. Breast tumors do not manifest a binary presence or absence. Instead, they fall on a continuum of size from large to microscopic, and only become detectable when they reach a size that matches the detectability threshold of a specific mammography technology. There will always be breast tumors that are below the detectability threshold of current mammography techniques but might become detectable using an improved mammographic technique that produces significantly increased radiographic contrast.

However, the performance of the proposed CEESM technology should not only be judged on its anticipated improvement in detecting breast cancer compared to CMRI or CEDM. CMRI and CEDM are not primarily intended as mammographic screening tools per se, but are intended as second-tier diagnostic procedures to resolve ambiguities in screening mammographic findings. The enhanced radiographic contrast rendition anticipated with the proposed CEESM technology could eventually provide a better tool for screening procedures as well as the ability to more clearly display lesion shape, edge characteristics, internal anatomy, etc., all of which can contribute to more accurate characterization of breast lesions.

The CEDEM technique as currently practiced clinically utilizes molybdenum and rhodium X-ray spectra generated at different voltages and modified by aluminum, molybdenum, and rhodium filters to optimize radiographic contrast following dual-energy subtraction imaging. Unfortunately, the physics of this 'adapted' technology is not ideally suited to dual-energy imaging when iodine is used as a contrast element. FIG. 2 from Lewin (5) shows how the two Mo and Rh X-ray spectra are positioned with respect to the k-edge of iodine. It can be seen that the 'high' and 'low' energy X-ray spectra are not well separated and do not optimally straddle the iodine k-edge.

Figure 3:
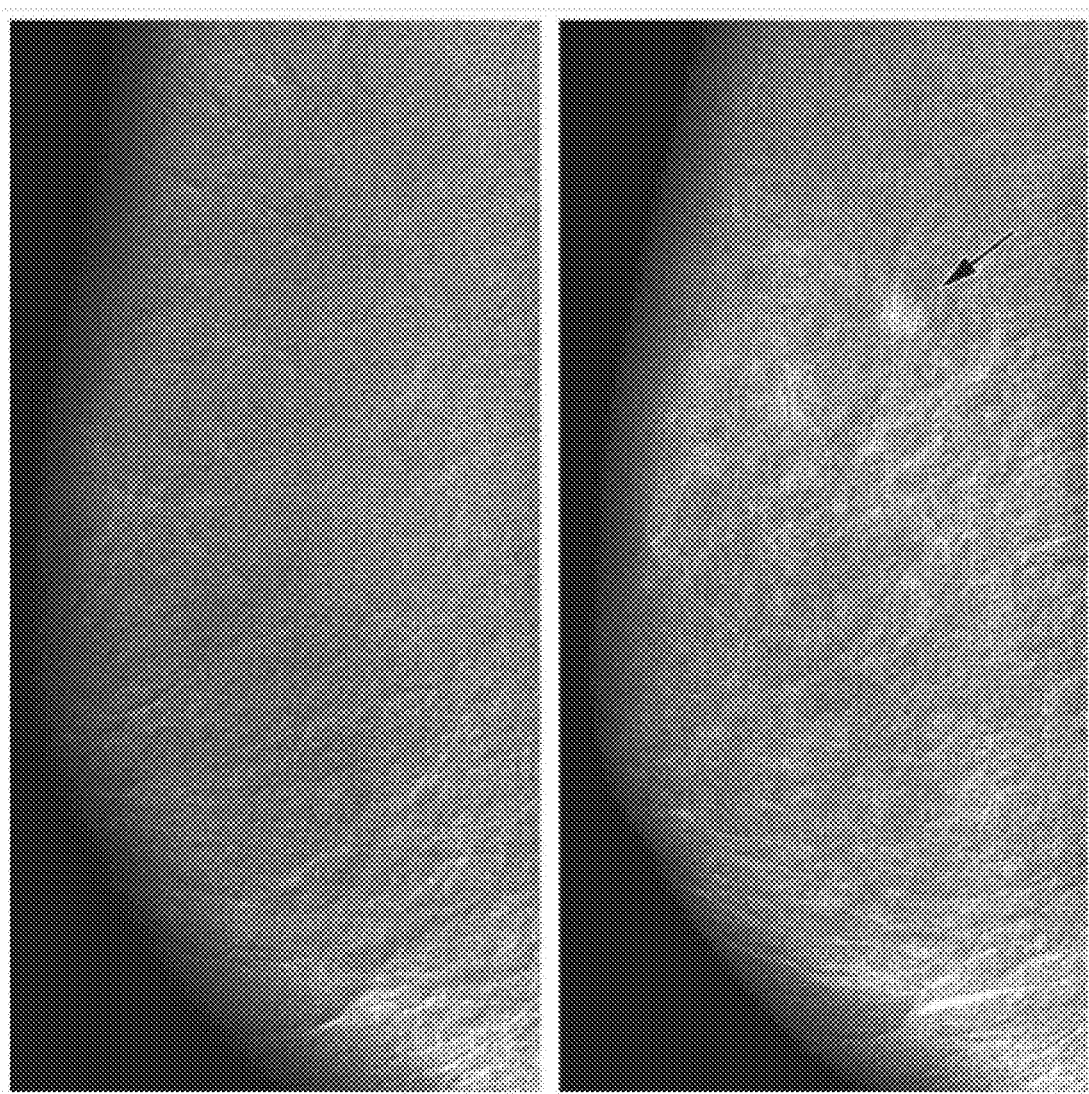
FIG. 3 shows mammographically and clinically occult tubular carcinoma (5-mm diameter). Left: Dual-energy CEDEM subtraction image shows a view very similar to a conventional screening mammogram. Right: Dual-energy CEDEM image shows enhancement of the cancer (arrow) with far greater contrast than the image on the left.

Despite the unavoidably sub-optimal subtraction, the mammograms obtained using the CEDEM technique are very impressive. FIG. 3 shows a clinical subtraction image from Lewin (5). The left panel shows a 'conventional' mammogram in which the tumor is essentially invisible. The right panel shows a subtraction mammogram in which the clutter of the surrounding, underlying, and overlying breast tissue has been greatly suppressed, making it very easy to see the tumor (shown by the arrow).

The presently disclosed CEESM technology displays radiographic contrast of breast tumors that is approximately 5 times greater than with the CEDEM technique. To appreciate the impact of such an improvement, FIG. 4 shows two simulated breast 'tumors'. The contrast difference between them is a factor of 5. The differences between the three separate panels is only the degree of statistical noise that has been progressively added to the simulated tumor images. The point to be made is that with a 'normal' amount of statistical noise (top panel), there is no doubt that both tumors are easily detectable, but with a large amount of statistical noise added (bottom panel), only the higher contrast tumor is detectable. The additional statistical noise could be more heterogeneous surrounding breast tissue or higher quantum noise due to a lowering of the radiation dose to the breast. This simulated example illustrates the potential diagnostic value of the CEESM technology.

The CEESM technology is based on two X-ray target elements, tellurium (Te) and cerium (Ce), chosen such that their characteristic X-ray energy distributions cleanly 'straddle' the k-edge of iodine and thereby optimize the radiographic contrast of iodine following dual-energy subtraction.

1. Choice of X-Ray Target Elements

In addition to the requirement of optimally distributed characteristic X-ray energies, the choice of suitable target elements depends on the physical properties of these materials as related to their mechanical and thermal characteristics.

When bombarded by electrons, all elements produce characteristic X-rays whose energies primarily depend on the binding energies of the K, L, and M shell electrons. The strategy applied to identify optimal target elements for the CEESM technology was to examine the electron binding energies of a number of potential candidate elements, and from that assessment to calculate the energies of the characteristic X-rays produced when those elements are bombarded by electrons of 50 keV energy. From this analysis, two elements that produced characteristic X-rays that exactly straddle the k-edge of iodine at 33.16 keV, as well as possess physical properties that would qualify them as suitable X-ray target materials were identified—tellurium (Te) and cerium (Ce).

FIG. 5 tabulates the characteristic X-ray energies of Te and Ce and the k-edge energy of iodine. FIG. 6 tabulates some relevant physical properties of Te and Ce as well as of Mo and Rh for comparison purposes. Mo and Rh were the standard X-ray target elements used in earlier years for general screening mammography and are currently the X-ray target elements used for contrast-enhanced dual-energy mammography such as in the CEDEM technique.

Figure 7:
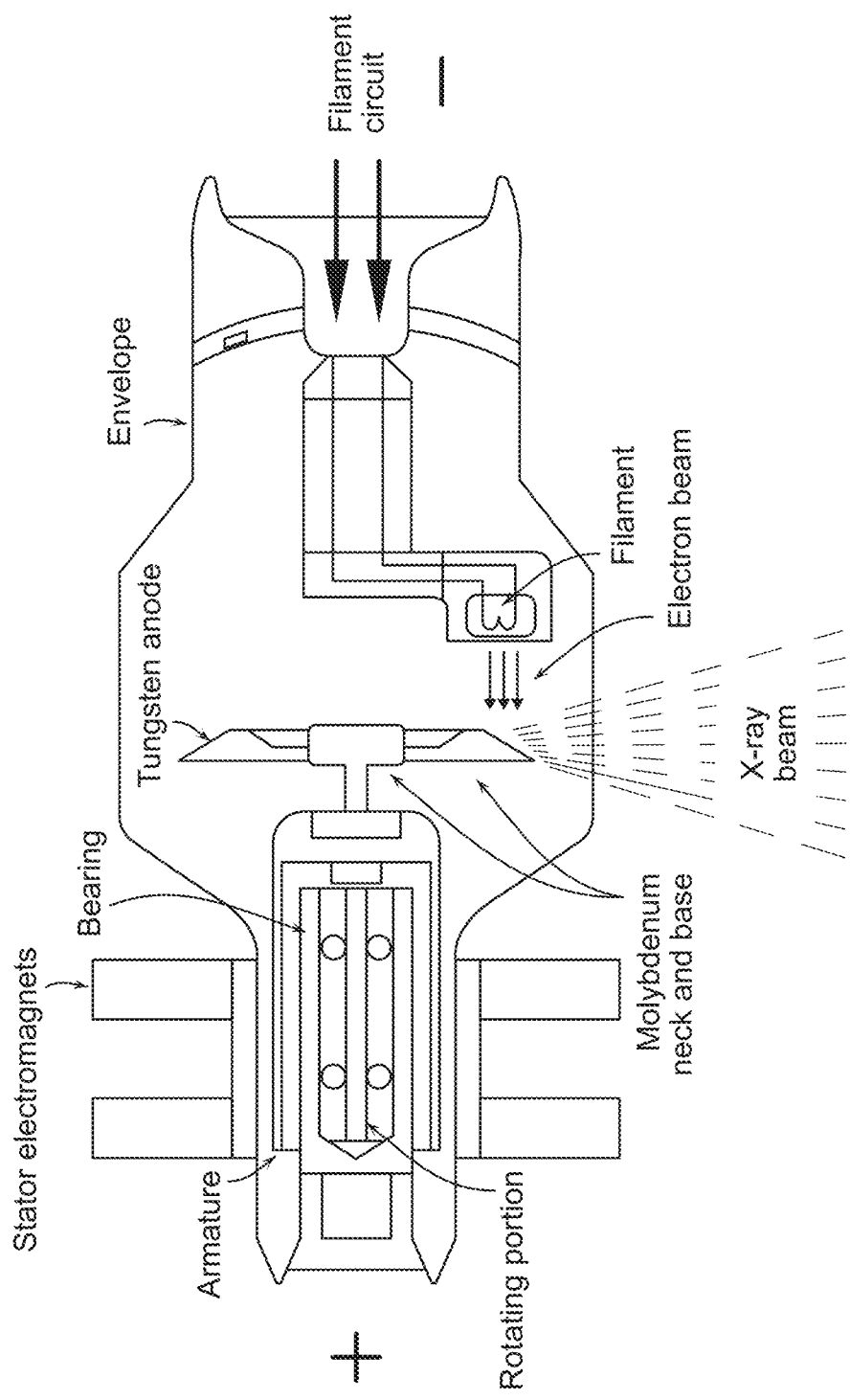
FIG. 7 shows attenuation coefficient of iodine as a function of X-ray energy showing the k-edge occurring at 33.16 keV.

FIG. 7 shows the mass attenuation coefficient of iodine as a function of X-ray energy. The attenuation coefficient is high at low X-ray energies and decreases rapidly down to the iodine k-edge at 33.16 keV. At the iodine k-edge energy, the X-ray attenuation of iodine rises vertically by a factor of about 6, and thereafter slowly decreases again with further increase in X-ray energy.

Commercial available contrast media containing iodinated contrast agents are usually classified as ionic monomers such as diatrizoate (marketed, e.g., under the trade mark Gastrografen™), ionic dimers such as ioxaglate (marketed, e.g., under the trade mark Hexabrix™) nonionic monomers such as iohexol (marketed, e.g., under the trade mark Omnipaque™) iopamidol (marketed, e.g., under the trade mark Isovue™), iomeprol (marketed, e.g., under the trade mark Iomeron™) and the non-ionic dimer iodixanol (marketed under the trade mark Visipaque™). The clinical safety of iodinated X-ray contrast media has continuously been improved over the recent decades through development of new agents; from ionic monomers (Isopaque™) to non-ionic monomers (e.g., Omnipaque™) and non-ionic dimers (e.g., Visipaque™).

Iodine was chosen many decades ago as the optimal element for X-ray contrast studies (replacing Thorotrast—a contrast agent based on the element thorium) due to the fact that the target element for producing diagnostic X-rays that was used then (and still is today) was tungsten, and for the most common tungsten X-ray spectra used for standard X-ray contrast studies the iodine k-edge conveniently overlaps with the peak intensity of a tungsten X-ray spectrum resulting in maximum radiographic contrast. However, for contrast-enhanced mammography, where the X-ray energies used are substantially lower than in conventional radiographic or fluoroscopic imaging due to the need to enhance the contrast of soft tissues and calcium microcalcifications, the iodine k-edge is 10-15 keV too high to result in optimized iodine contrast.

Two possible solutions could be applied to resolve this issue:

1) A new contrast element could be developed with a k-edge of 10-15 keV below that of iodine—at approximately 20 keV. This solution would require the design, development, and clinical testing of a completely new contrast agent, although one such agent, molybdenum-disulphide, was recently developed for an unrelated purpose (7). The k-edge of molybdenum in fact occurs at exactly 20 keV. U.S. Patent Application Publication No. US2017/62508159 discloses molybdenum as a new contrast element specifically for dual-energy contrast-enhanced mammography, and is incorporated herein by reference in its entirety.

2) The low and high energy X-ray spectra could be modified to optimally straddle the k-edge of iodine. This second solution is the basis of the present disclosure, which describes the use of two X-ray target elements, tellurium and cerium, that produce characteristic X-ray spectra optimized to exploit the k-edge of iodine.

FIG. 5 tabulates the characteristics X-ray energies of Te and Ce. The highest characteristic X-ray of Te is 30.98 keV, slightly below the 33.16 keV k-edge iodine, while the lowest characteristic X-ray of Ce is 34.28 keV (ignoring for the moment the Ce 4.80 keV X-ray), which is slightly above the k-edge of iodine.

FIG. 6 tabulates some relevant physical properties of Te, Ce, Mo, and Rh.

2. Mathematical Modeling of Te and Ce X-Ray Spectra

X-ray production by electrons bombarding a target material occurs through two separate mechanisms:

i. Bremsstrahlung X-Ray Production

Figure 10:
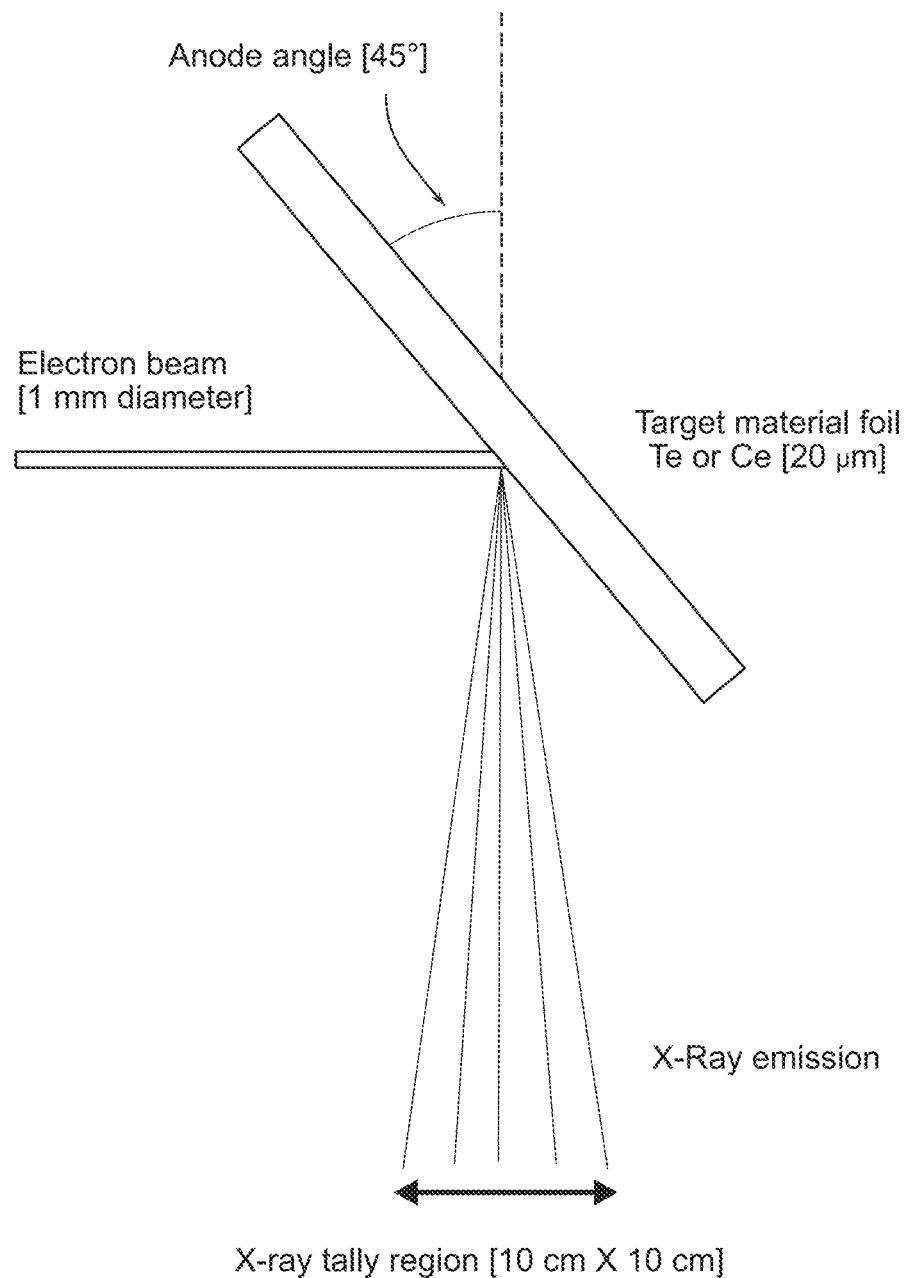
FIG. 10 shows a simplified mathematical model for computing Te and Ce X-ray spectra.

This process is illustrated in FIG. 10. An incident electron (e.g., number 1, 2, or 3) passes close to a target element's nucleus. Due to the electrostatic attraction between the negative electron and the positive nucleus, its trajectory is deviated towards the nucleus where it absorbs a small amount of additional energy from the atom, which for the purposes of energy conservation it must immediately re-emit. It does so by emitting an X-ray photon called a 'bremsstrahlung' ('braking-radiation' in German) X-ray. The greater the electron's deviation, the higher will be the energy of the emitted X-ray. The bremsstrahlung X-rays so produced populate a continuous energy spectrum from zero up to the original energy of the incident electron.

ii. Characteristic X-Ray Production

Figure 8:
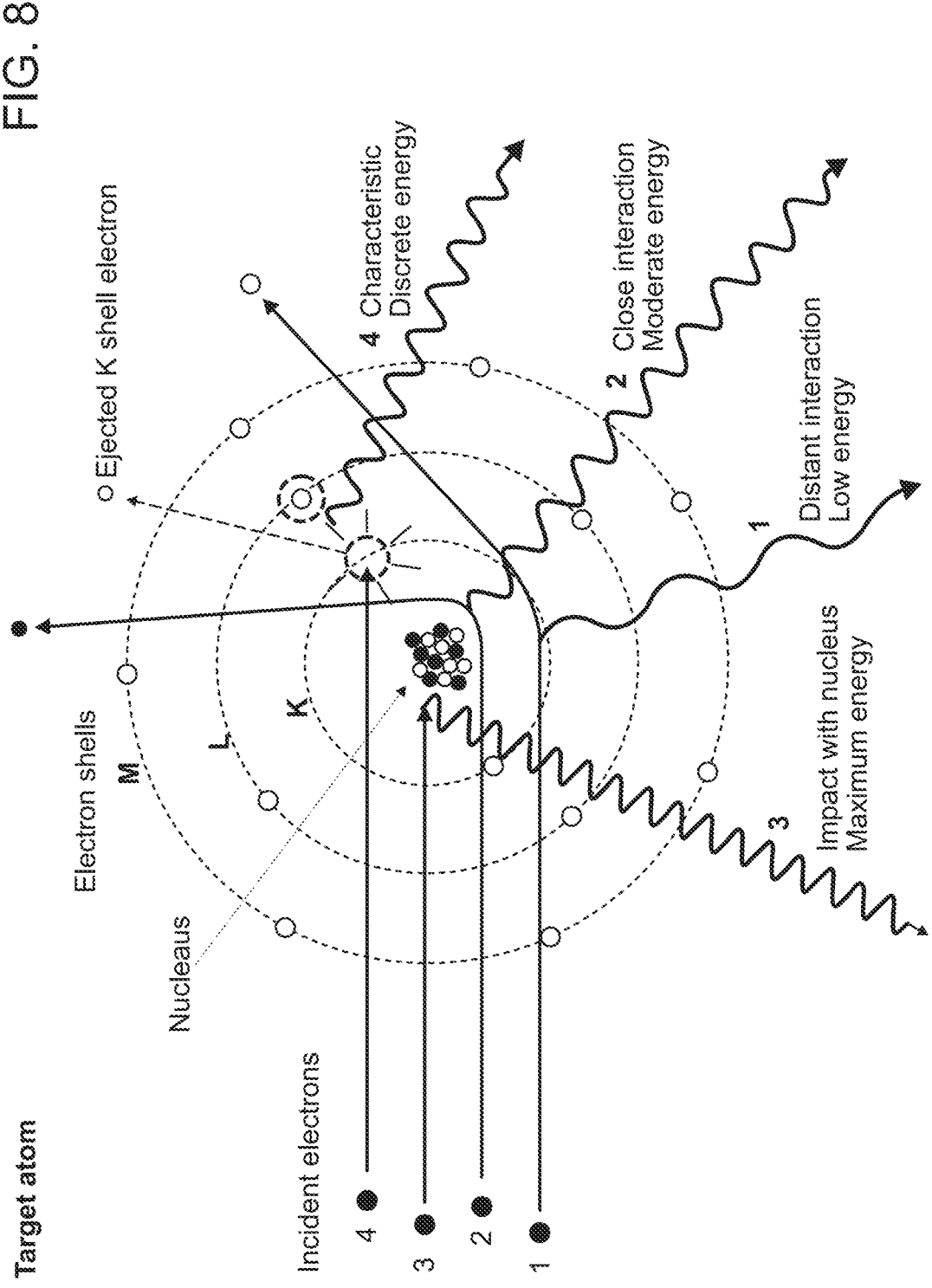
FIG. 8 shows an illustration of bremsstrahlung and characteristic X-ray production in a target material atom.

This process is illustrated in FIG. 8. An incident electron (electron 4) knocks one of the more tightly-bound electrons (typically in the K- or L-shells) out of the atom. The vacancy created is immediately filled by an electron from a higher level shell, and in the process the difference in binding energy between the two shells is emitted as an X-ray photon called a 'characteristic X-ray'.

Whereas bremsstrahlung X-ray spectra are continuous and do not contain a 'fingerprint' of their element of origin, characteristic X-ray spectra are discrete and uniquely reflect their element of origin. For target materials having similar atomic numbers to those of Te and Ce, the relative intensities of bremsstrahlung and characteristic X-ray production are very roughly equal. Therefore, any theoretical calculations that utilize X-ray spectra emitted by elements within this window of atomic numbers need to take into account both bremsstrahlung and characteristic X-rays. Consequently, much more detailed X-ray spectra produced by Te and Ce need to be known in order to enable accurate mathematical modeling.

There are no data in the scientific or technical literature relating to X-ray spectra produced by target elements other than tungsten, molybdenum, or rhodium. Therefore, to develop technology of the present disclosure, it was necessary to compute de novo the characteristic X-ray spectra for Te and Ce from first principles. This was done using a publicly accessible computational code called MCNP4 (9).

Figure 9:
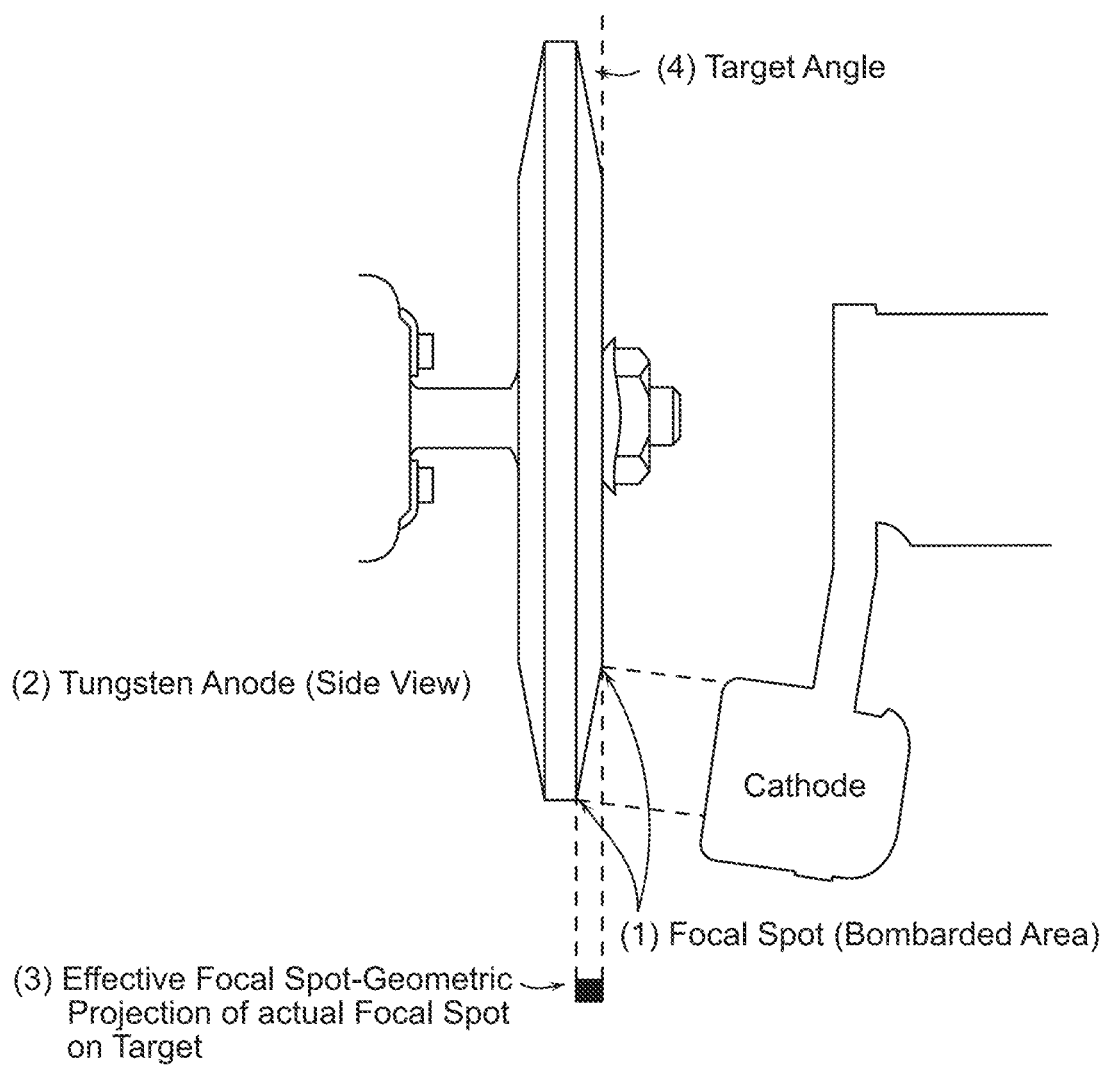
FIG. 9 shows an illustration of an electron beam impinging on the surface of a conventional rotating anode.

A diagram of an electron beam impinging on the surface of a conventional rotating anode is shown in FIG. 9. The three short arrows emanating from the filament in the cathode depict the side view of an electron beam of rectangular cross-section that bombards the surface of the anode.

A simplified mathematical model corresponding to the geometry in FIG. 9 is shown in FIG. 10 and was used to calculate the Te and Ce X-ray spectra. The target elements were 20 µm thick foils of Te and Ce mounted on the surface of a molybdenum anode. The electron beam had an energy of 50 keV and the emitted X-rays were observed at an average angle of 900 to the axis of the electron beam and at an angle of 450 to the emitting surfaces of the Te and Ce foils.

Figure 11:
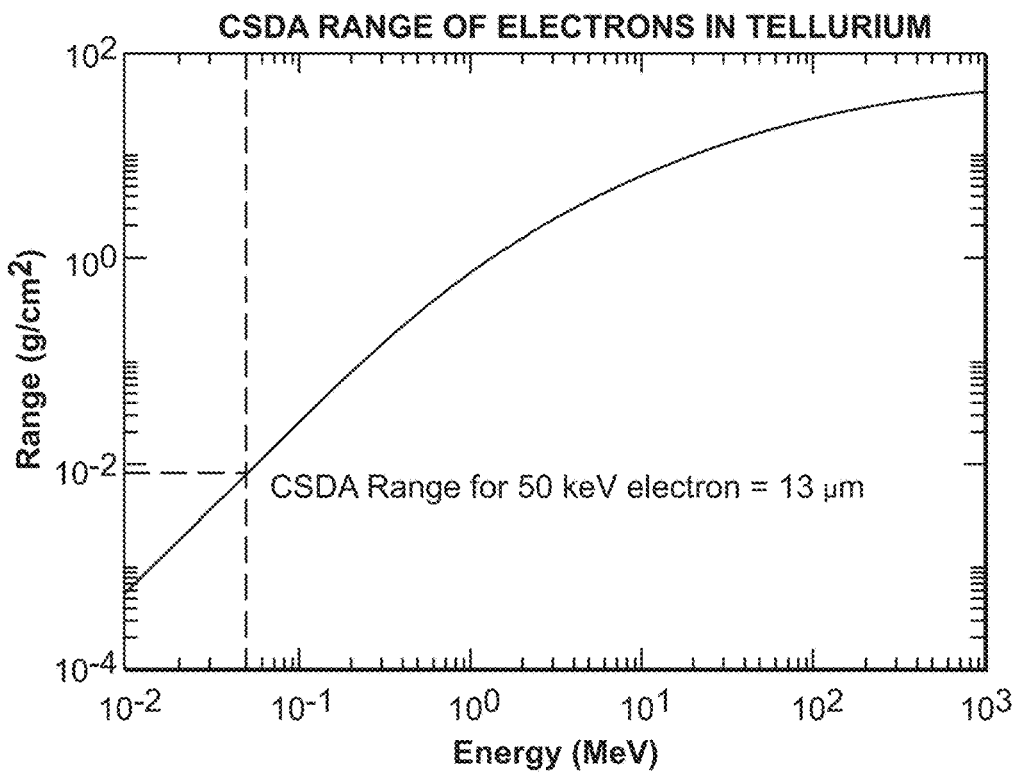
FIG. 11 shows CSDA range of 50 keV electrons in tellurium foil.
Figure 12:
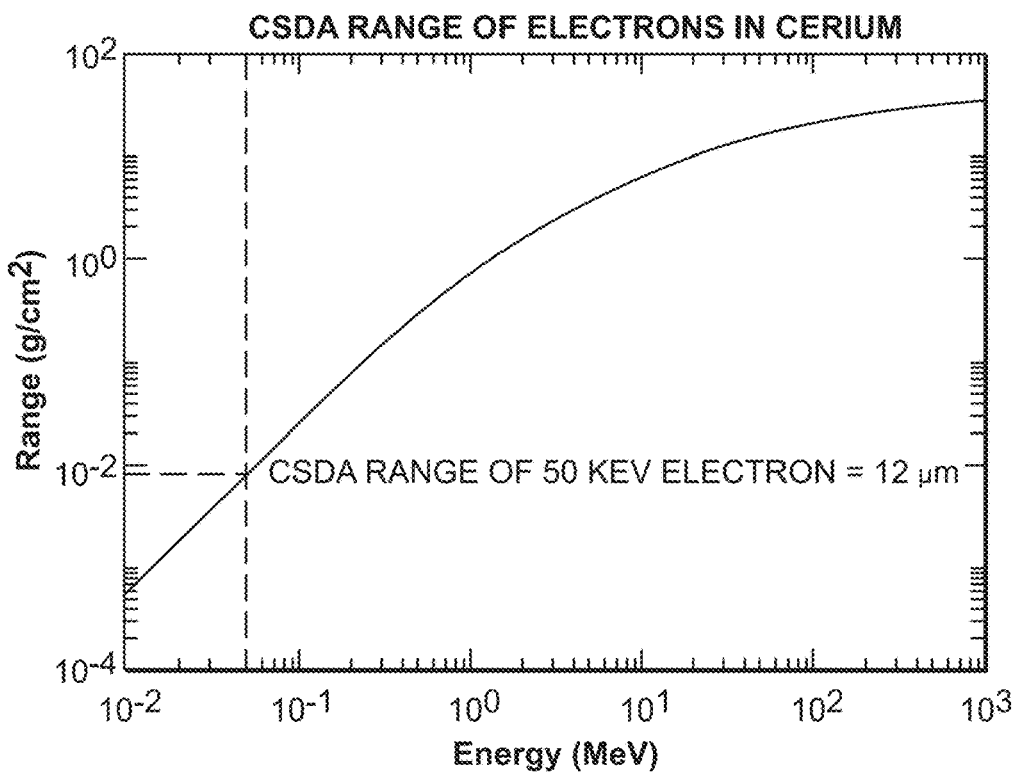
FIG. 12 shows CSDA range of 50 keV electrons in cerium foil.

To maximize heat transfer from the Te and Ce foils to the molybdenum anode body, it is desirable to make the foils sufficiently thin so that they only slightly exceed the range of the electrons bombarding them. FIG. 11 & FIG. 12 show the 'continuous-slowing-down-approximation' (CSDA) range of electrons in Te and Ce (11). From these graphs, a 50 keV electron has a range of 13 µm in Te and 12 µm in Ce. Consequently, the mathematical X-ray production model assumed a foil thickness of 20 µm for both Te and Ce. These are also foil thicknesses that can readily be purchased.

Figure 13:
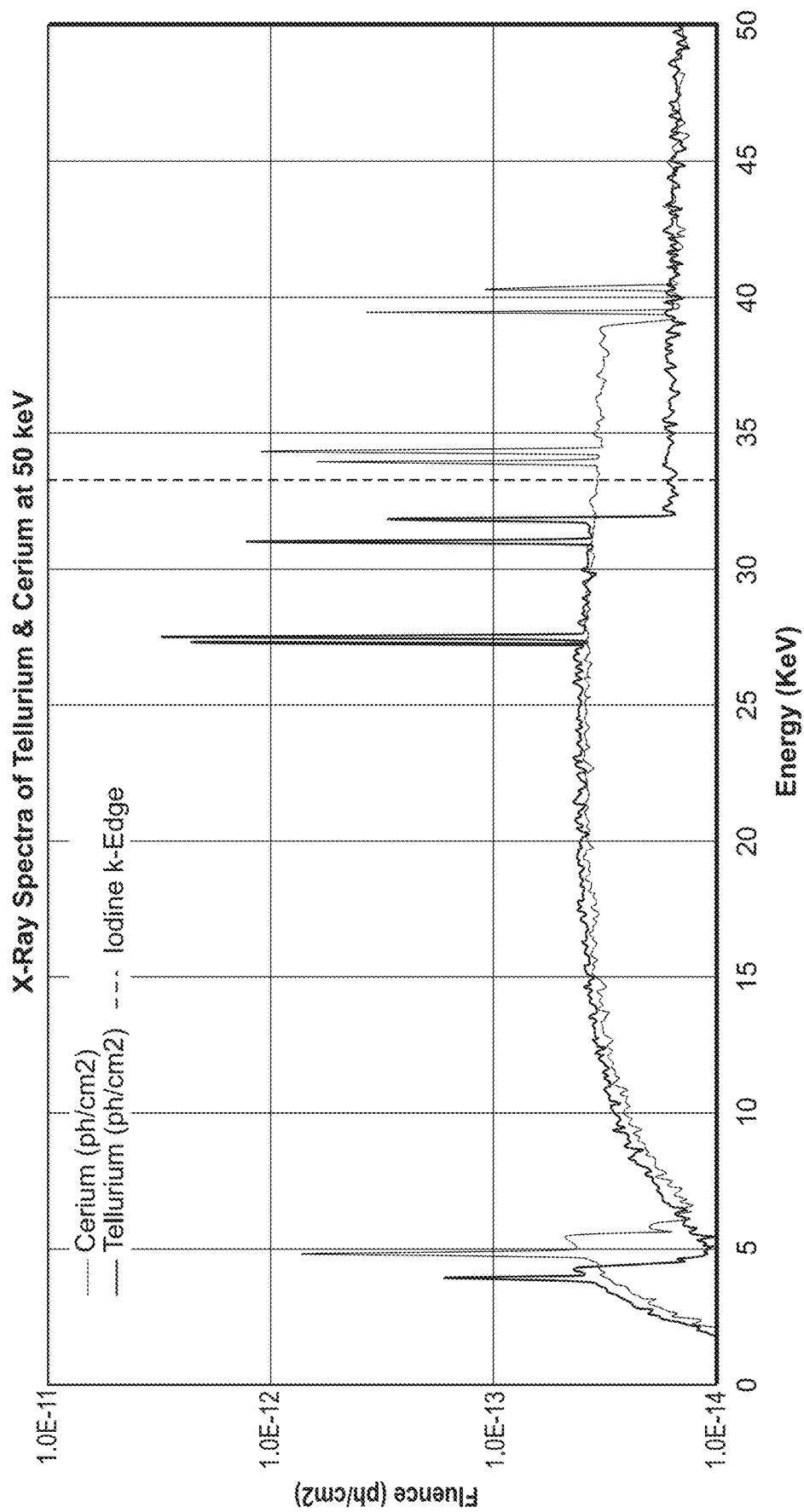
FIG. 13 shows X-ray spectra from Te and Ce produced by 50 keV electron bombardment, normalized to one incident electron.

Te and Ce were selected as target materials primarily on the basis of their distribution of characteristic X-rays with respect to the k-edge of iodine. The Te and Ce calculated X-ray spectra are shown in FIG. 13. The characteristic X-rays of Te are all located to the left of the iodine k-edge while all those of Ce are located to the right. Under these conditions, the difference in X-ray attenuation between the Te and Ce spectra is maximized. The characteristic X-rays produced by Te and Ce at very low energies of 3-5 keV are irrelevant in the present context, since to minimize radiation dose to the breast in mammography filters are employed that selectively suppress most of the X-ray spectrum below about 20 keV. For the CEESM technology, similar filters could be employed which would also preclude the 3-5 keV characteristic X-rays of Te and Ce from making any contribution to image formation.

In addition to possessing characteristic X-rays at the required energies, it is important for the selected target elements to possess physical properties that would make them realistically useable as X-ray sources for mammographic imaging. Some relevant physical properties of Te and Ce (density, melting point, and specific heat) are listed in FIG. 6.

The higher the density of the target material, the thinner the foil can be made while still accommodating the entire range of the impinging electron beam. A thinner foil provides more efficient conductivity of heat from the foil to the molybdenum anode body.

The melting points of Te and Ce are, respectively, about 4 times and 2 times lower than those of Rh. Rh is a well-established target element used ubiquitously for mammographic imaging prior to the introduction of digital mammography and currently implemented in the GE Seno-Bright™ system, so it serves as a useful example of an acceptable X-ray target element.

There are two design changes that could be implemented to compensate for the lower melting points of Te and Ce compared to Rh:
1) The cathode filament, whose long dimension together with the anode angle determine the projected length of the 'effective' focal spot, can be doubled in length and the anode angle halved. This adjustment would produce an effective focal spot of the same projected size but with a factor of 2× greater heat capacity.
2) The diameter of the focal-spot track on the rotating anode can also be doubled, which would increase the effective heat capacity by a further factor of approximately 2.

Therefore, combining these relatively simple design changes, a 4× increase in the heat capacity of the Te and Ce target foils could be achieved, effectively bringing them up to the same approximate heat capacity of the reference Rh target.

However, two downsides would result from these modifications:
1) Due to the reduction in anode angle, the so-called 'heel effect' would produce a less uniform X-ray intensity distribution.
2) Due to the increase in focal-spot track diameter, the physical size of the X-ray tube insert would need to be increased.

While not desirable, these two disadvantages would not necessarily impact the performance of an X-ray tube modified as described above.

With regard to specific-heat, Te, Ce, and Rh specific-heat parameters are quite similar for all three materials.

In summary, both Te and Ce have acceptable physical properties with respect to their use as X-ray target materials for the CEESM technology.

Before describing the results of the mathematical modeling related to the CEESM technology, the principle of radiographic contrast enhancement by image subtraction will be illustrated.

Figure 14:
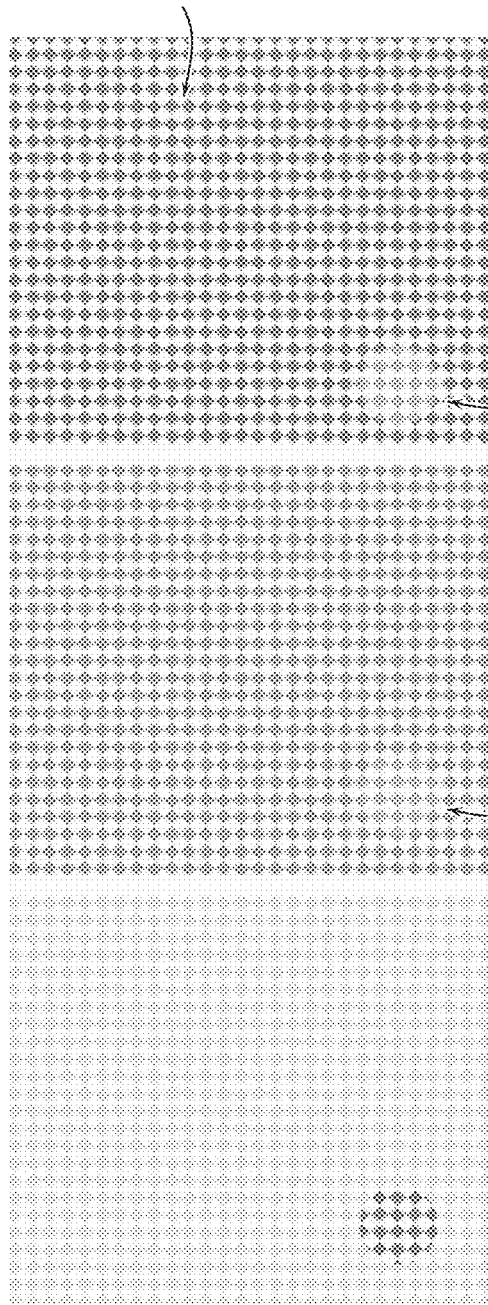
FIG. 14 shows an illustration of the principle of contrast enhancement through image subtraction.

Referring to FIG. 14, the X-ray image at the top represents a mammogram of a breast containing a tumor (the tumor can be seen in the bottom right-hand corner of this image), containing a relatively low concentration of iodine. This image is obtained with the lower energy Te X-ray spectrum. On a relative basis, normal breast tissue or blood is assumed to contain 33% of the contrast agent in the tumor (i.e., the tumor/blood contrast agent ratio is 3:1). The tumor is difficult to see for the following three reasons: 1) The low iodine concentration within the tumor; 2) because the characteristic X-rays of Te are to the left of the iodine k-edge, i.e., where the iodine attenuation is at its lowest level; and 3) because the anatomical clutter produced by the surrounding normal breast tissue (illustrated by the stippling pattern) blurs out the edges of the tumor. The X-ray image in the middle is obtained with the slightly higher energy Ce X-ray spectrum. The tumor is seen a little more clearly because the characteristic X-rays of Ce are to the right of the iodine k-edge where the iodine attenuation is about 6 times higher than to the left. The bottom X-ray image shows the result of subtracting the top and middle images from each other. The anatomical clutter of the surrounding breast tissue is significantly suppressed by the subtraction process producing much clearer visibility of the tumor.

3. Mathematical Modeling Validating the CEESM Technique.

Figure 17:
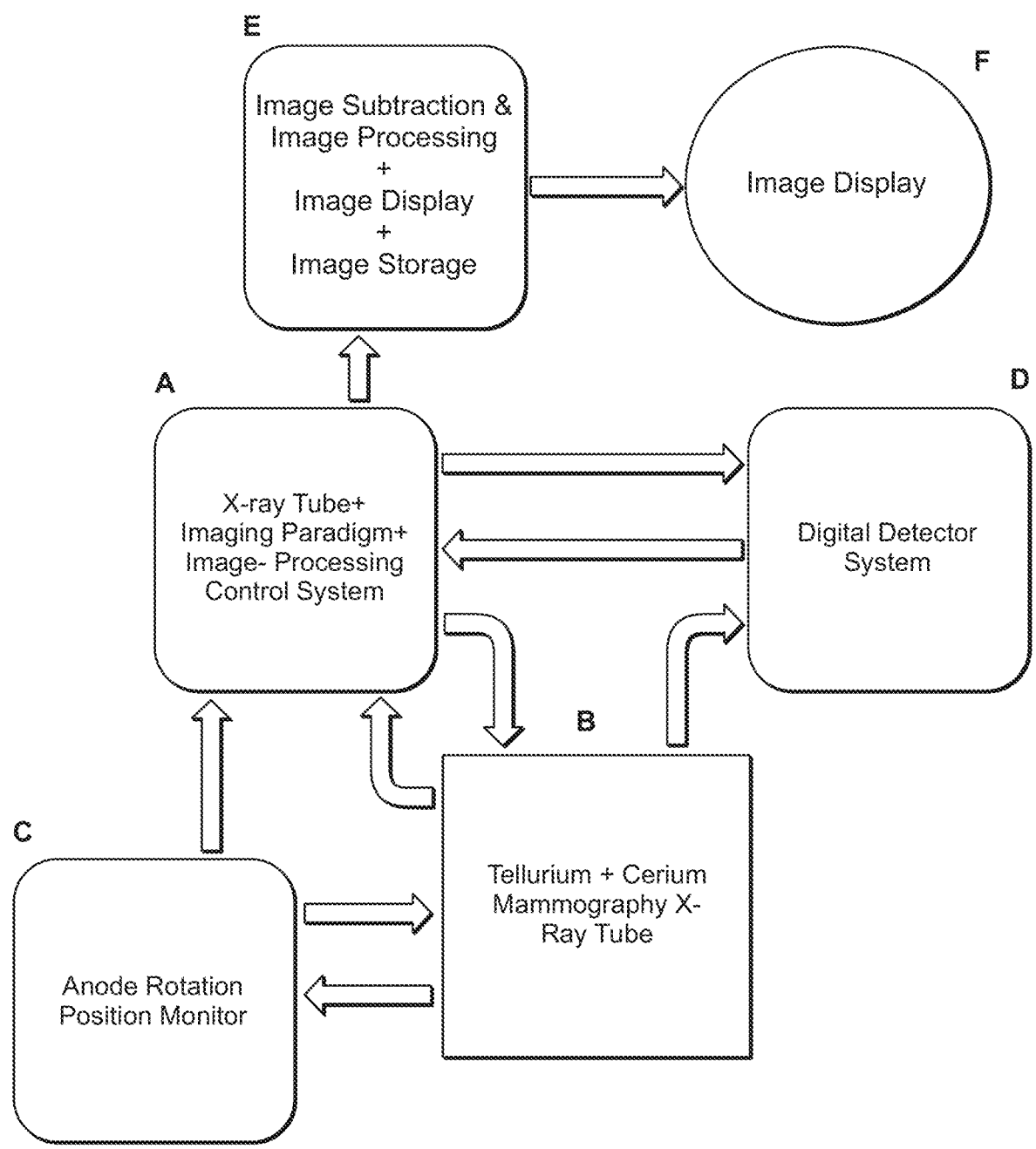
FIG. 17 shows a process control diagram for CEESM technology.

FIG. 17 shows the mathematical model used to validate the CEESM technology. The same mathematical model was used to evaluate the imaging characteristics of the existing clinically practiced CEDEM technique so that the advantages of the CEESM technology could be demonstrated relative to the current state-of-the-art.

The rectangle represents a breast containing a 'background' concentration of iodinated contrast agent. The physical equivalent of this image could be the concentration of iodine in normal breast tissue or in blood following contrast administration to the patient. The tumor is modeled as a cylinder of 1 cm depth containing a higher concentration of iodine. The two concentrations are related through the 'tumor/blood ratio'. The two dependent variables that are calculated using this model are the radiographic contrast and the coefficient-of-variation (CV). These two parameters are explained below:

i. Coefficient of Variation (CV)

The CV is the statistically combined standard deviations of the number of photons represented by the fluences f1 and f3, divided by their mean, and usually expressed as a percentage.

When Te and Ce X-rays produce images of iodine distribution inside a breast, four signal components are produced by the digital detector:
1) A signal corresponding to Te X-rays passing through 'background' iodine in normal breast tissue and iodine inside the 1 cm-thick tumor (f3);
2) A signal corresponding to Te X-rays passing only through background iodine in the normal breast tissue (f1);
3) A signal corresponding to Ce X-rays passing through background iodine inside normal breast tissue and iodine inside the 1 cm-thick tumor (f4);
4) A signal corresponding to Ce X-rays passing only through background iodine in the normal breast tissue (f2).

A simplifying assumption made was that all X-rays striking the detector elements are absorbed with equal efficiency.

The mathematical formalism employed to calculate radiographic contrast and coefficient of variation (CV) is given below:

$$Ce\ \text{CONTRAST} = 2[f2 - f4]/[f2 + f4]$$

$$Te\ \text{CONTRAST} = 2[f1 - f3]/[f1 + f3]$$

-continued $$DE \text{ CONTRAST} = 2[f4 - f3] - [f2 - f1]/[f4 - f3] + [f2 + f1]$$

$$DE/Ce \text{ CONTRAST} = [[f4 - f3] - [f2 - f1]/[f4 - f3] + [f2 - f1]]/[[f2 - f4]/[f2 + f4]]$$

$$DE/Te \text{ CONTRAST} = [[f4 - f3] - [f2 - f1]/[f4 - f3] + [f2 - f1]]/[[f1 - f3]/[f1 + f3]]$$

$$CV = 2\sqrt{[[\phi_1 + \phi_2 + \phi_3 + \phi_4]/[\phi_1 - \phi_2] - [\phi_3 - \phi_4]]^2 + [[\phi_1 + \phi_2 + \phi_3 + \phi_4]/[\phi_1 - \phi_2] - [\phi_3 - \phi_4]]^2}$$

ii. Radiographic Contrast

Radiographic contrast is the difference in intensities of the X-ray beams passing through normal breast tissue and tumor and through only surrounding normal breast tissue. Mathematically, the radiographic contrast is expressed as a ratio. For example, referring to FIG. 15, for the Te X-ray beam, the radiographic contrast RC is given by:

$$RC = 0.5*[f1 - f3]/[(f1 + f3)]$$

As used herein, the term "about" means that the numerical value for x has a range ±5% of the recited numerical value, unless specified otherwise. For example, when a described embodiment or a claim recites rotating frequency of "3,600 rpm", this is to be understood to mean a rotating frequency from 3,420 rpm to 3,780 rpm.

In certain aspects, the present disclosure relates to an apparatus for X-ray mammography, comprising an X-ray tube, wherein the X-ray tube comprises: an anode, and a focal spot track, wherein the focal spot track comprises a tellurium foil and a cerium foil.

In some embodiments, the anode is a rotating molybdenum alloy anode, wherein the rotating frequency of the anode is from about 3,600 rpm to about 10,000 rpm.

In some embodiments, the tellurium foil and the cerium foil are attached to the anode.

In some embodiments, the tellurium foil is in a shape of 180° semicircular annular strip, and the cerium foil is in a shape of 180° semicircular annular strip, wherein the tellurium foil and the cerium foil contact each other, and the tellurium foil and the cerium foil are oriented with respect to each other to form a circle.

In some embodiments, the radius of each of the 180° semicircular annular strips is from about 10 mm to about 100 mm. In some embodiments, the radius of each of the 180° semicircular annular strips is about 50 mm.

In some embodiments, the tellurium foil and the cerium foil is each independently from about 5 μm to about 50 μm thick. In some embodiments, wherein the tellurium foil and the cerium foil is each about 20 μm thick. In some embodiments, wherein the tellurium foil and the cerium foil is each about 13 μm thick.

In some embodiments, the apparatus further comprises a filament adapted to emit an electron beam, and the width of the filament is from about 0.1 mm to about 0.5 mm, such as about 0.3 mm.

In some embodiments, the anode is adapted to emit an X-Ray beam, wherein an angle between the rotation axis of the anode and the central axis of the X-Ray beam is from about 3° to about 9°. In some embodiments, the anode is adapted to emit an X-Ray beam, wherein an angle between the rotation axis of the anode and the central axis of the X-Ray beam is about 6°.

In some aspect the present disclosure relates to an image acquisition and X-ray generation control system, comprising:
a first control system adapted to initiate and terminate rotation of an anode and heating of a filament;
a second control system adapted to apply and remove a voltage of about 50,000 volts between the anode and the filament;
an X-Ray tube comprising a focal spot track, wherein the focal spot track comprises tellurium and cerium, and wherein the X-Ray tube is adapted to produce tellurium and cerium X-ray production pulses with a start time and a stop time for each pulse;
a monitor adapted to synchronize rotation of the anode to the start and stop times of the tellurium and cerium X-ray production pulses; and
an image processing module adapted to:
generate tellurium and cerium dual-energy image pairs,
scale and subtract the tellurium and cerium dual-energy image pairs, thereby generating image data,
store the image data, and
transmit the image data to an image display module.

In some aspect the present disclosure relates to a method of X-ray imaging of a tissue in a subject, comprising: administering to a subject an iodine-based contrast agent; positioning the subject in the apparatus; and acquiring an image of the tissue of the subject.

In certain embodiments, the tissue is breast tissue.

EXAMPLES

Instrumentation

The instrumentation required to implement the CEESM technology consists of an existing mammography system, such as those manufactured primarily by General Electric, Siemens, Philips, Toshiba, Fuji, and Hologic. The required modifications mostly center on the redesign of the X-ray tube, tube housing, and digital exposure control systems. The design modifications are described in more detail below.

Example 1. Tellurium and Cerium Foils

Tellurium and cerium foils are available in 99.9% purity from the Goodfellow Corp., in thicknesses of 5 μm up to 2 mm. The cost of a 20 μm-thick 5×5 cm Te or Ce foil is about $2,500.

Figure 18:
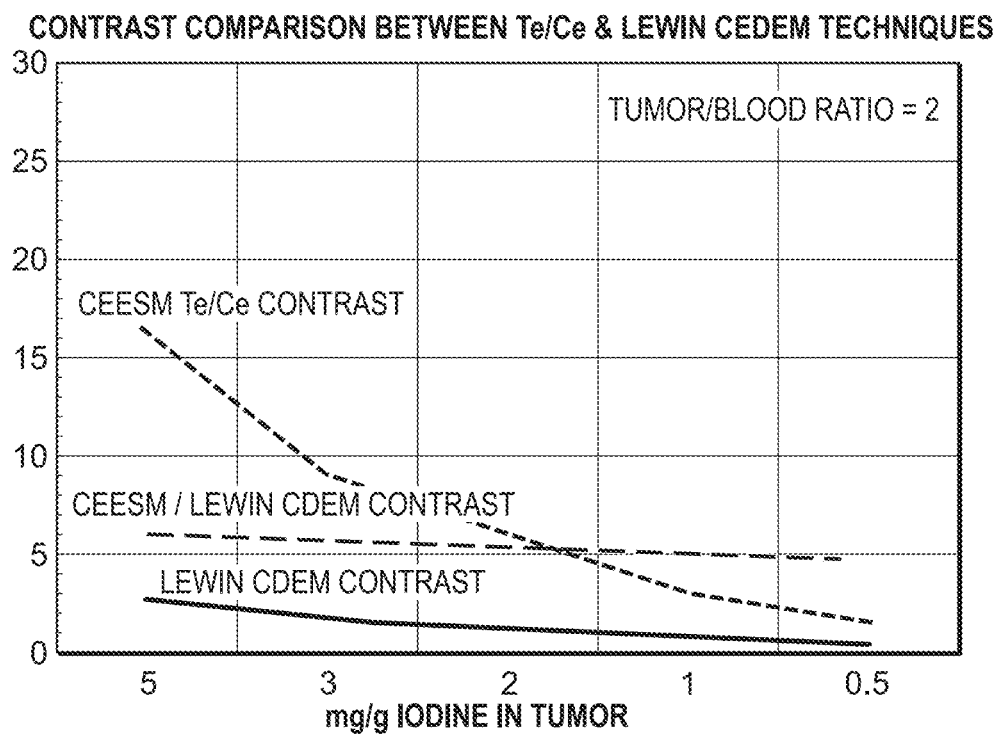
FIG. 18 shows a radiographic contrast comparison between CEDEM and CEESM technologies for tumor/blood ratio 2.

The thickness of the tellurium and cerium foils should be at least 13 μm, which corresponds approximately to the range of a 50 keV electron in those materials. Thicker foils would not affect the X-ray spectra produced but could have some impact on the amount of power that could be delivered by the electron beam to the foils without causing thermal damage. FIG. 18 shows the proposed method by which the Ce and Te foils would be attached to a molybdenum anode. The visual perspective presented is along the line-of-sight of the electron beam that leaves the filament in the cathode and impinges on the surface of the tellurium or cerium foil. The cross-section of the electron beam with a doubled filament length would be about 0.3 mm×10 mm. The 0.3 mm dimension corresponds to the width of the filament, which translates directly to the width of the X-ray focal-spot. The length of the X-ray focal spot is foreshortened geometrically according to the Sine of the anode angle and is designed to project an effective focal-spot length of 0.3 mm. Therefore, with an anode angle of 60, the effective X-ray focal-spot size would be 0.3 mm×0.3 mm, which is the size usually used in conventional contact mammography.

Example 2. Heat Management

The anode body is rotated during X-ray exposure at a rotational speed of 3,600 rpm (the most common rotational speed used in mammographic X-ray tubes). This effectively 'sweeps' the rectangular impact area of the rectangular electron beam in a circular trajectory around the periphery of the rotating anode body and thereby increases the effective area of impact of the electron beam by a factor of ηD, where D is the center-to-center diameter of the focal-spot track. Assuming a 100 mm diameter focal-spot track—approximately double that used in conventional mammography X-ray tubes—anode rotation would reduce the relative heating of the Te and Ce foils affixed to the anode surface by a factor of 100η—or about 300× (assuming the X-ray exposure time is exactly equal to the time for one revolution of the anode). One revolution of the anode corresponds to 16.7 ms at 3,600 rpm. Since such short exposure times are almost never used in conventional mammography, from a practical perspective with more typical exposure times of about 100 ms there will be an overlap of the area of the anode surface exposed to the electron beam by a 'repainting' factor of roughly 6×. Repainting still continues to reduce the heating effect of the electron beam since the focal-spot track cools down substantially during each anode rotation. In practice, X-ray tube manufacturers make focal-spot track 'cooling-curves' available to users, which provide safe exposure guidelines for a wide range of exposure conditions. A doubling of the anode diameter would significantly increase the size of the X-ray tube housing but would not introduce any insurmountable geometric issues.

Example 3. Digital Signal Management

Two methods can be used to alternate the X-ray exposures between Te and Ce X-ray emissions:

1) In the current design of mammography units that utilize molybdenum and rhodium X-ray targets to produce two X-ray beams of slightly differing energy (such as the GE SenoBright™ system and others), the Mo and Rh focal-spot tracks along the periphery of the anode are concentric and displaced from each other in radius by a millimeter or less. There are two separate filaments in the cathode each designed to individually focus the electron beam on either the Mo or the Rh focal-spot track for the entire exposure period.

Advantages of this approach are: 1) The X-ray production during a complete mammographic exposure is constant placing less demands on digital signal processing systems. 2) The electron beam current can be differentially varied between the two target materials to optimally 'balance' the digital signal levels for Mo and Rh exposures under different exposure scenarios.

Disadvantages of this approach are: 1) The spatial location of the effective X-ray focal-spot marginally shifts between Mo and Rh exposures, potentially causing a minor spatial mismatch in the subtraction images. 2) Since the dual-energy exposures are separated from each other by a much longer period of time (typically on the order of 100-300 ms), this can potentially result in more breast motion or vessel pulsation artefacts in the subtraction images.

2) An alternative approach is shown the design illustrated in FIG. 18, in which the two target foils are mounted on the anode body surface at the same radius and divided into two 180° arcs.

Because the Te and Ce X-ray beams would alternate during every half-rotation of the anode (i.e., every 8-9 ms in the case of 3,600 rpm anode rotation speed), there would be optimal spatial correlation between the Te and Ce images as well as much greater immunity to breast motion and vessel pulsation artefacts.

There are, however, three potential disadvantages of this second approach: 1) Due to the rapid alternation between Te and Ce exposures, greater engineering demands are placed on the bandwidth and other design factors of the digital imaging system. 2) The balancing of the Te and Ce digital signals is more complicated because the electron-beam current would need to be monitored and modulated on a time-scale of 8-9 ms. 3) The use of different filter materials for the Te and Ce exposures would be precluded; however, calculations to be presented shortly indicate that different filter materials would most likely not be necessary.

Example 4. Control Architecture

The control architecture of the proposed patent is illustrated in FIG. 17. Without resorting to unnecessary detail, the sequential control steps following a command to initiate a mammographic exposure would proceed as follows:
1) Control System (A) instructs X-Ray Tube (B) to initiate filament heating and anode rotation.
2) Control System (A) instructs X-ray Tube (B) to apply high-voltage to the anode. Te and Ce X-rays produced in alternating sequence by X-ray tube (B) are transmitted through the patient's breast to digital detector (D).
3) Digital Detector (D) transmits image sequence to control system (A), and anode rotation position monitor (C) transmits the sequence of Te and Ce tagged images to control system (A).
4) Control System (A) synchronizes tagged Te and Ce images and transmits them to image subtraction and image processing module (E).
5) Image subtraction & image processing module (E) scales and subtracts Te & Ce image pairs, stores all image data, and sends subtracted and digitally enhanced images to image display module (F).

Example 5. Mathematical Validation Calculations

The mathematical calculations to validate the CEESM technology assume a nominal concentration of 0.5 mg of iodine per g of blood or normal breast tissue. This was based on the CEDEM technique (5) as currently implemented in the GE SenoBright™ mammography system.

The CEDEM protocol involves injection of 350 mg of iodine/ml in 100 ml of solution. For a 60-70 kg individual, this translates to an average concentration of about 0.5 mg of iodine/g of tissue. There will no doubt be significant variations in the iodine concentrations in different tissues and at different post-injection times, but in the absence of more specific data it was assumed that the concentration of 0.5 mg/g would apply to normal breast tissue and/or blood.

In the case of a breast tumor that absorbs more iodine due to neovascularity and other influences of tumor biology, an average tumor/blood ratio of 3:1 has been assumed. This was based on data from (10) which used diffuse correlation optical spectroscopy to determine tumor and normal breast tissue blood flow in human breast tumors. An average tumor/normal breast tissue blood-flow ratio of 2.7 was measured in this study. Therefore, the present calculations were carried out assuming a rounded-up tumor/blood iodine concentration ratio of 3:1, an iodine concentration in blood and normal breast tissues of 0.5 mg/g, and a corresponding iodine concentration in tumor of 1.5 mg/g. Additional scoping calculations were carried out using iodine tumor/blood ratios of 2:1, 3:1, and 5:1, and tumor iodine concentrations of 0.5 mg/g, 1 mg/g, 2 mg/g, 3 mg/g, and 5 mg/g.

A number of elements were tried out as filters for the Te and Ce X-ray beams. A filter thickness of 7 μm of silver finally was chosen because it produced excellent radiographic contrast enhancement, and also because it was a close-to-optimal filter for both Te and Ce X-ray beams, fulfilling the requirement mandated by the proposed X-ray tube design.

Air KERMA values were computed from the X-ray fluxes exiting the model of the breast, and where necessary converted to average glandular breast dose. As used herein, the term "KERMA" refers to kinetic energy released per unit mass, defined as the sum of the initial kinetic energies of all the charged particles liberated by uncharged ionizing radiation (i.e., indirectly ionizing radiation such as photons and neutrons) in a sample of matter, divided by the mass of the sample. Air KERMA is used for the traceable calibration of gamma instrument metrology facilities using a "free air" ion chamber.

Figure 15:
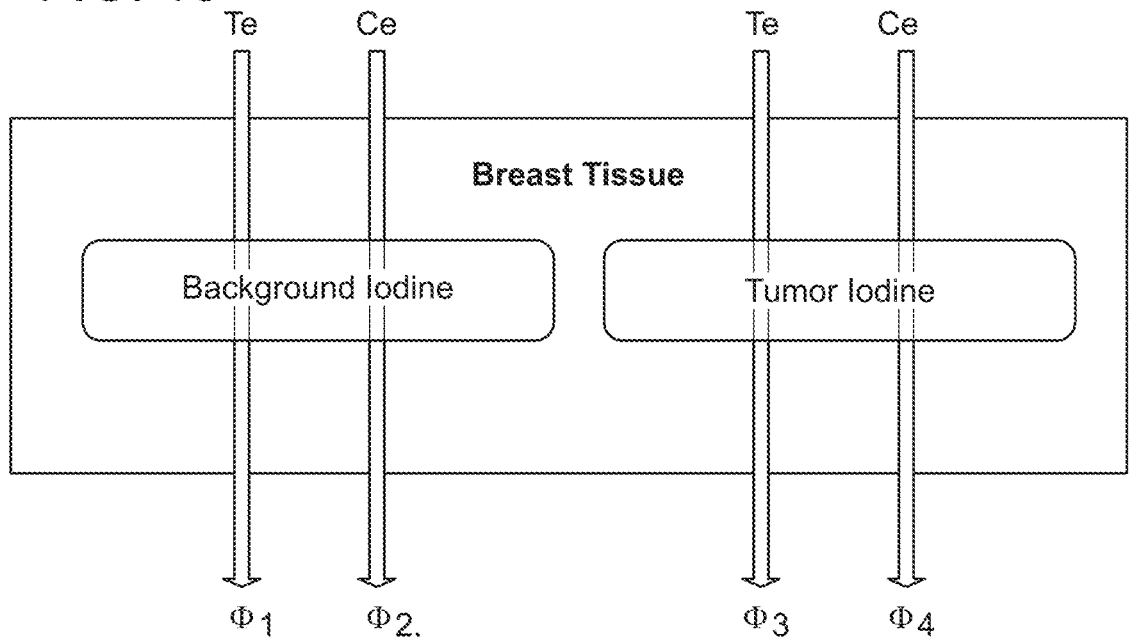
FIG. 15 shows a mathematical model to validating the CEESM technique.
Figure 16:
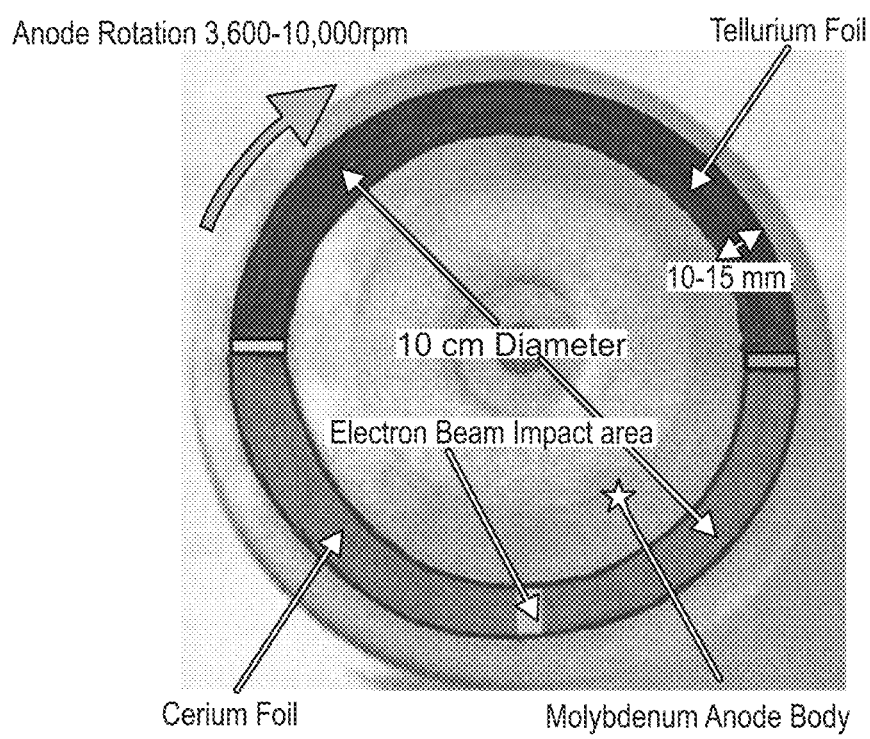
FIG. 16 shows an illustration of how the tellurium and cerium foils are mounted to the surface of a molybdenum anode. As the anode rotates at 3,600 rpm, the electron beam impact area sweeps along each foil in turn alternating the production of Te and Ce X-rays.

Seven independent variables are related to the mathematical model shown in FIG. 15, and are listed below with the range of their assigned values in parentheses including their 'nominal' values:
1. Iodine concentration in tumor (1.5 mg/g; 0.5-5).
2. Iodine concentration in normal breast tissue or blood (0.5 mg/g; 0.1-2.5).
3. Iodine tumor-to-blood ratio (3:1; 2:1-5:1).
4. Kilovoltage (50 kVp).
5. Silver filter thickness (0.007 mm).
6. Compressed breast thickness (50 mm; 30-80).
7. Air KERMA (1.0 mGy; 1-15).

Five calculated dependent variables are listed below:
1. Radiographic contrast for tellurium X-ray exposure.
2. Radiographic contrast for cerium X-ray exposure.
3. Radiographic contrast for the CEESM dual-energy exposure.
4. Coefficient-of-variation (CV) of the CEESM dual-energy radiographic contrast values.
5. Air KERMA values for a range of breast dose conditions.

In addition to using the described model to perform calculations for the CEESM technology, the same model was used to calculate radiographic contrast parameters for the GE SenoBright system. This was done to produce a more objective assessment of the degree of improvement of the CEESM technique over the current CEDEM technique. The parameters used for the CEDEM technique calculations were obtained from reference (5) and are listed below:

High-energy X-ray beam: 44 kVp, Rh target, 0.025 Rh filter, 8 mm Al filter;
Low-energy X-ray beam: 30 kVp, Mo target, 0.03 Mo filter;
Breast thickness: 50 mm;
Breast composition: 50% glandular/50% fat.

Because voltage settings and filters reported as optimal by Lewin for the implementation of the CEDEM technique were for a breast thickness of 50 mm, for fairness of comparison the present calculations comparing the radiographic contrast performance of the CEDEM and CEESM techniques were only done for a 50 mm breast thickness.

Figure 19:
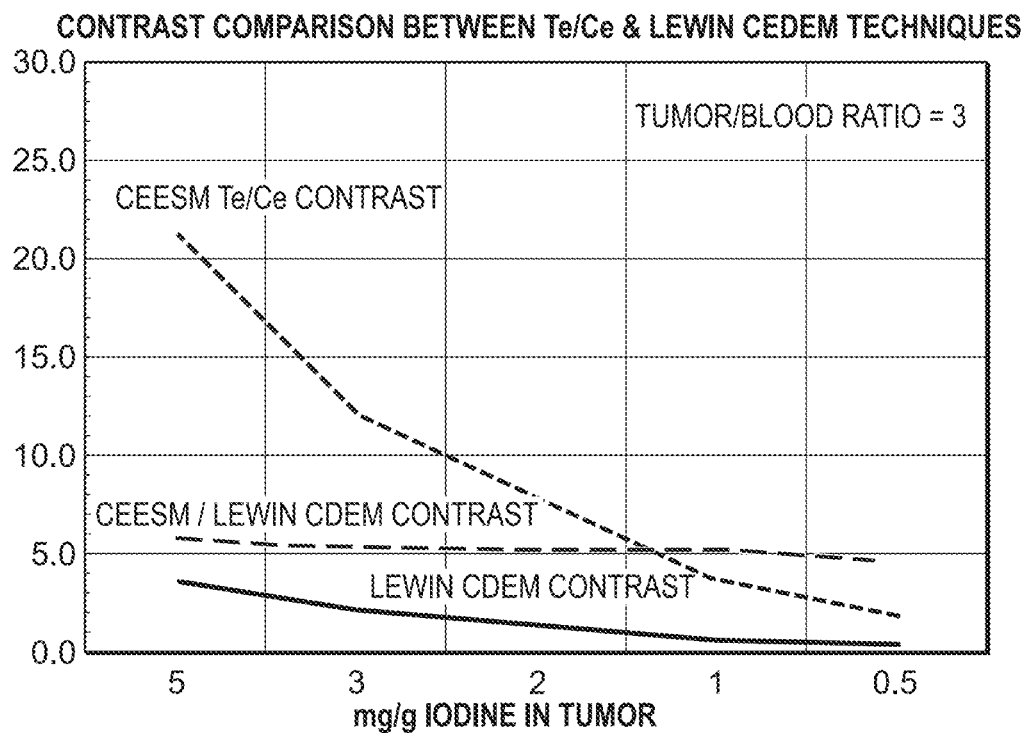
FIG. 19 shows a radiographic contrast comparison between the CEDEM and CEESM technologies for a 50 mm thick breast and a tumor/blood ratio 3.
Figure 20:
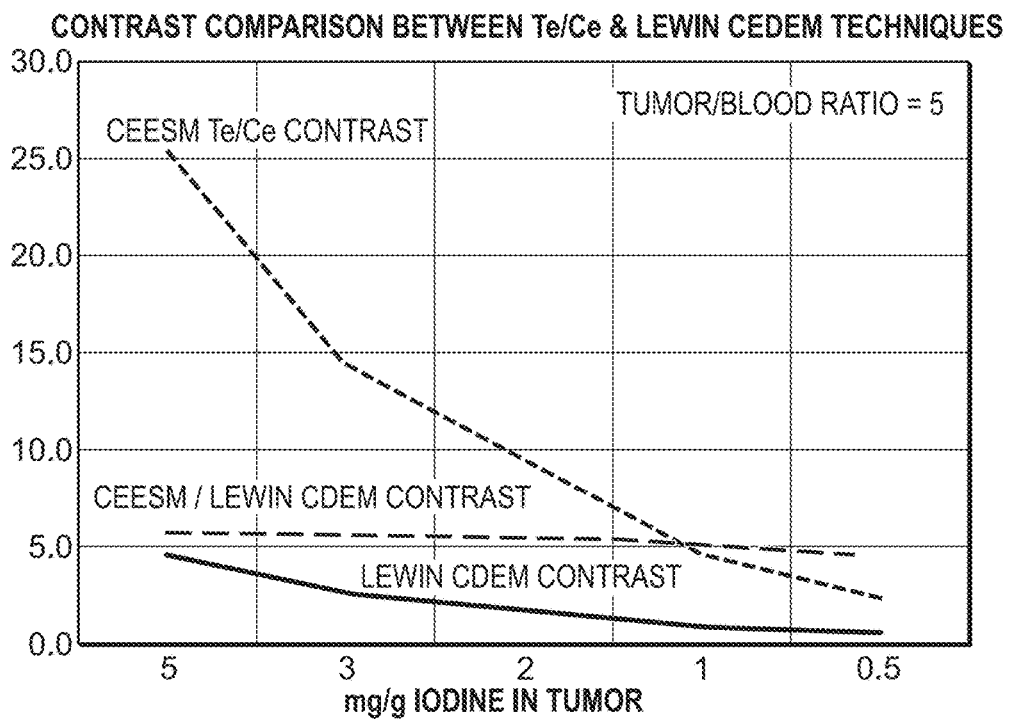
FIG. 20 shows a radiographic contrast comparison between CEDEM and CEESM technologies for tumor/blood ratio 5.

FIGS. 18, 19, and 20 show the comparison between the CEDEM and CEESM technologies for tumor/blood ratios of 2, 3, and 5 and tumor iodine concentrations of 0.5-5 mg/g. It can be seen that almost independently of either the tumor/blood ratio or the tumor iodine concentration, the radiographic contrast of the CEESM technique is about 5 times higher than the CEDEM technique.

Figure 21:
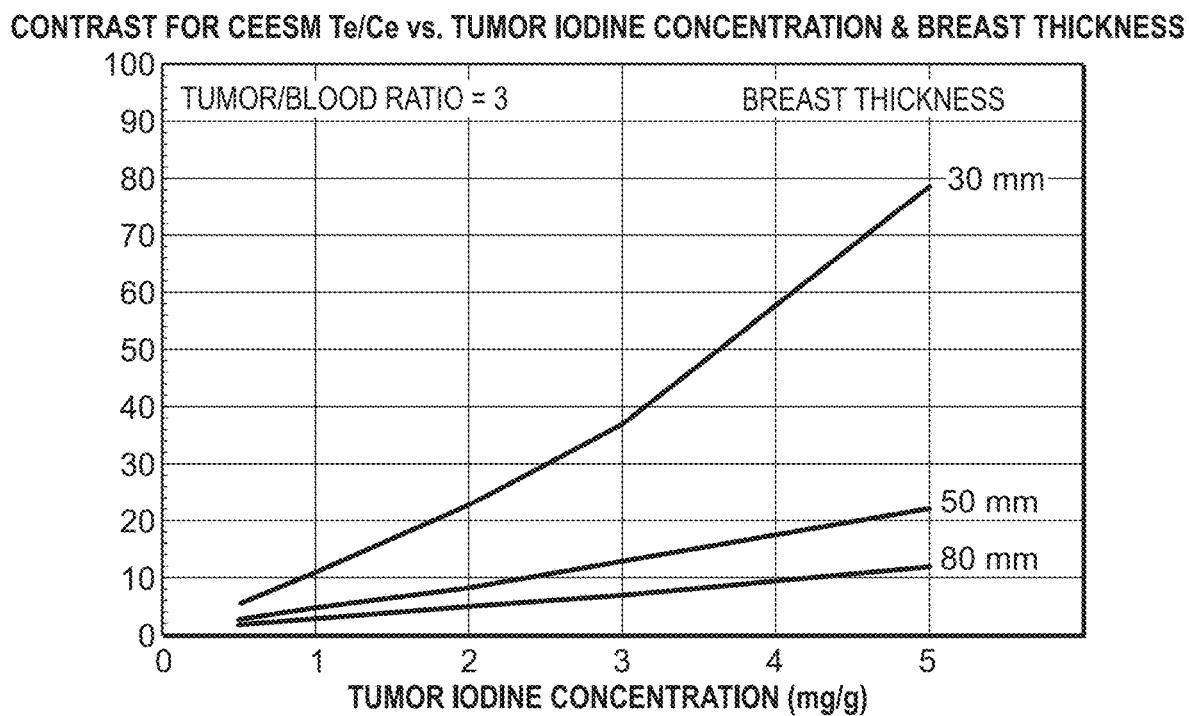
FIG. 21 shows a radiographic contrast vs. tumor iodine concentration for a tumor/blood ratio of 3 and breast thicknesses of 30 mm, 50 mm, and 80 mm.

FIG. 21 shows the radiographic contrast for the CEESM technique for three different breast thicknesses of 30 mm, 50 mm, and 80 mm vs. iodine concentrations in tumor for a tumor/blood ratio of 3. As would be expected, the radiographic contrast deteriorates with increasing breast thickness.

Figure 22:
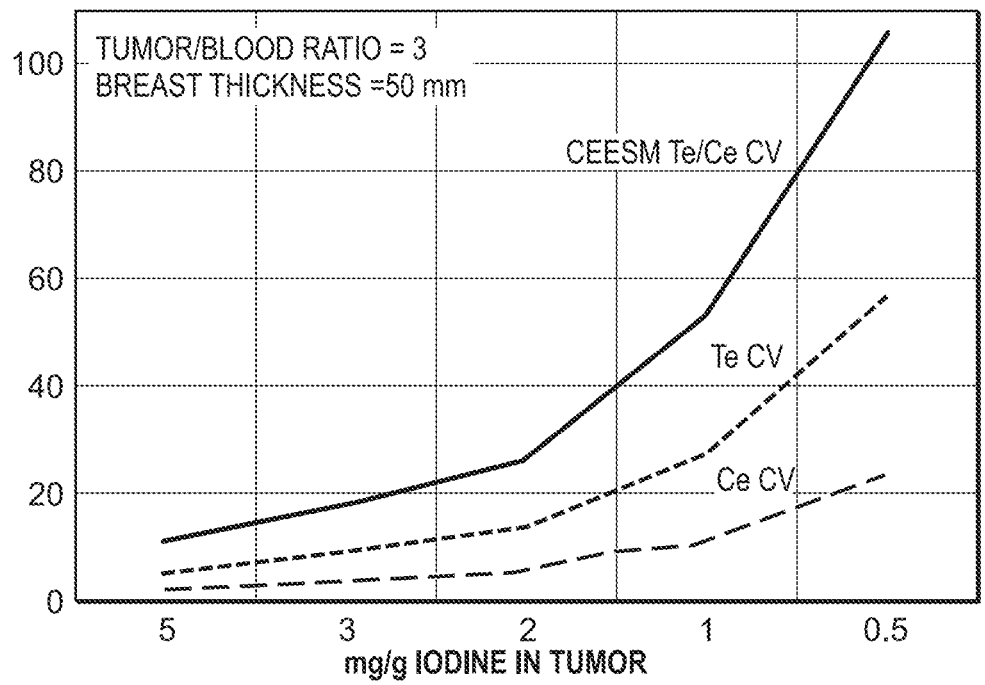
FIG. 22 shows a radiographic contrast for the CEESM technique for a breast thicknesses of 50 mm and a tumor/blood ratio of 3 vs. iodine concentration in tumor. Curves are also shown for single-energy Te and Ce X-ray beams.

FIG. 22 shows the radiographic contrast for the CEESM technique for a breast thickness of 50 mm and a tumor/blood ratio of 3 vs. iodine concentration in tumor. Curves are also shown for single-energy Te and Ce X-ray beams. The higher radiographic contrast evident for the Ce X-ray beam would be expected since the Ce X-rays primarily interact on the high-energy side of the iodine k-edge.

Figure 23:
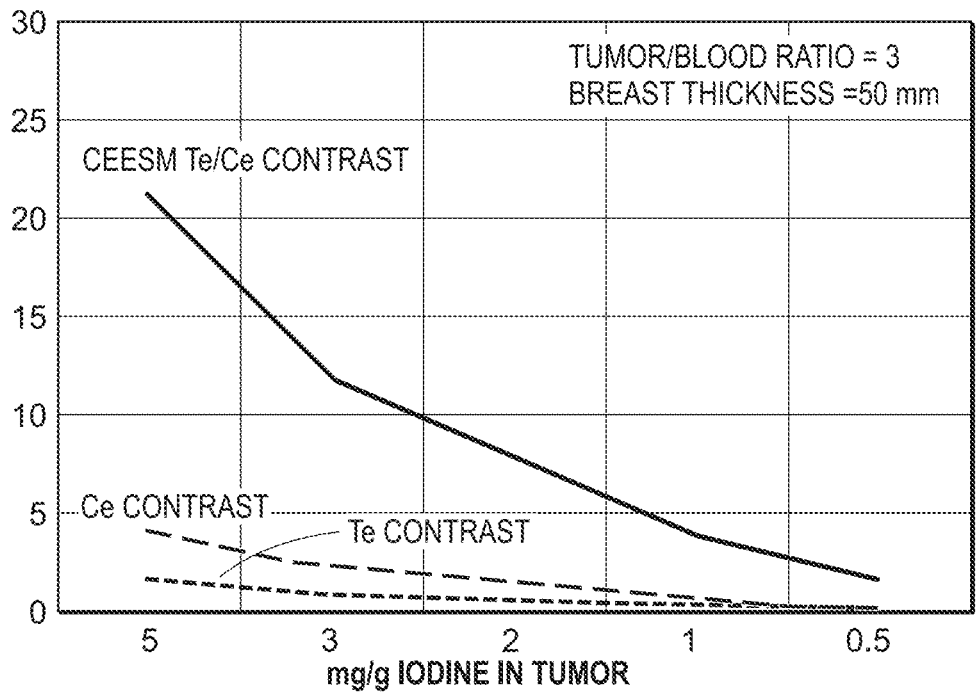
FIG. 23 shows a coefficient of variation (CV) for the CEESM technique and single-energy Te and Ce X-ray beams vs. iodine concentration in tumor for a breast thickness of 50 mm and a tumor/blood ratio of 3.

FIG. 23 shows the %-coefficient-of-variation (CV) for the CEESM technique and single-energy Te and Ce X-ray beams vs. iodine concentration in tumor for a breast thickness of 50 mm and a tumor/blood ratio of 3. It can be seen that for all tumor iodine concentrations, the CV of the Te beam is substantially higher than the CV of the Ce beam. This is because for the present model no attempt has been made to adjust the Te and Ce X-ray exposure levels to optimize the CV of the final CEESM image. In general, approximately equal CVs for the individual Te and Ce X-ray beams would minimize the CV for the CEESM subtraction image. In the present example, this could be attained by decreasing the relative exposure of the Ce beam by about a factor of 4 (since CV varies as the square-root of the exposure).

Figure 24:
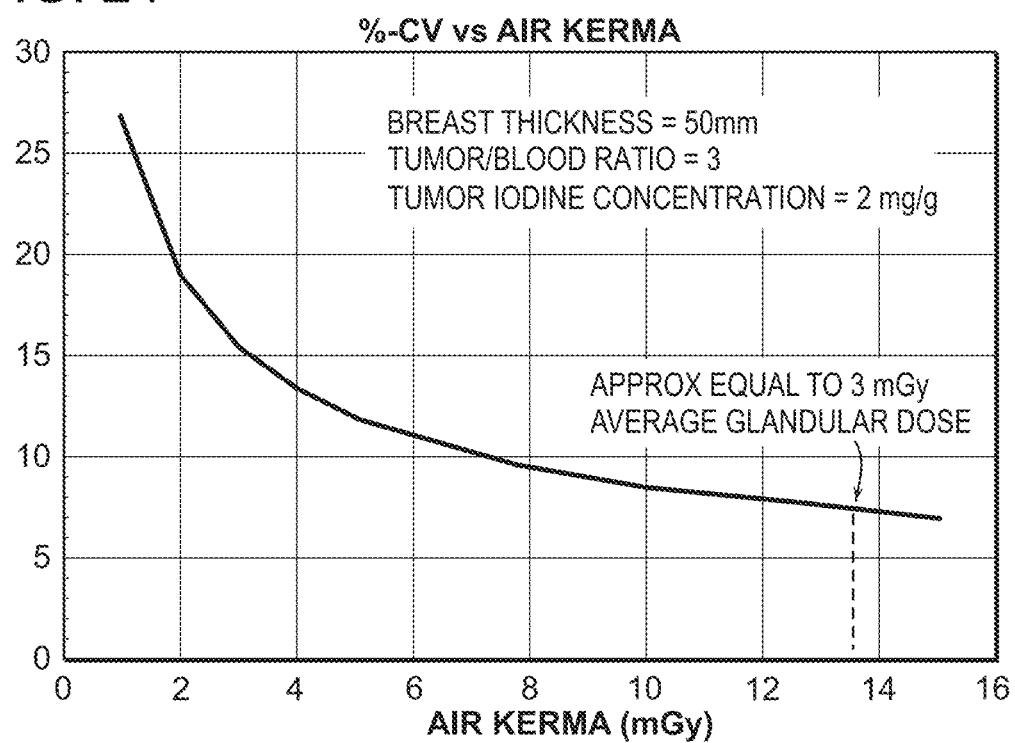
FIG. 24 shows a CV vs. Air KERMA for 50 mm breast, iodine concentration in tumor 2 mg/g, and tumor/blood ratio 3.

FIG. 24 shows the percent—coefficient of variation (CV) for the CEESM technique vs. Air KERMA for a breast thickness of 50 mm, tumor/blood ratio of 3, and tumor iodine concentration of 2 mg/g. For a 50 mm thick breast, an Air KERMA of 13.5 mGy is roughly equivalent to an average-glandular-dose (AGD) of 3 mGy—the maximum AGD permitted by the FDA.

To summarize the theoretical results disclosed herein, the calculated results for the CEESM technique indicate that, independently of iodine concentration or distribution, when compared to the clinically practiced CEDEM technique, equivalent to the imaging paradigm implemented in the GE SenoBright™ Spectral Mammography system, the CEESM technique yields radiographic contrast values for iodine that are approximately 5 times higher. Moreover, this is achievable with no increase in average glandular dose to the breast compared to the CEDEM technique. Therefore, the CEESM technology should be capable of detecting significantly smaller tumors and rendering anatomical details of tumors significantly more clearly than existing contrast-enhanced mammography techniques.

INCORPORATION BY REFERENCE

All U.S. patents and U.S. and PCT patent application publications mentioned herein are hereby incorporated by reference in their entirety as if each patent or publication was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES CITED

1. U.S. Cancer Statistics Data Visualizations Tool, based on November 2018 submission data (1999-2016): Centers for Disease Control and Prevention and National Cancer Institute; June 2019.
2. World J Clin Oncol 2014; 5(2): 61-70
3. Breast Care Basel 2010; 5(2):109-114
4. Am J Roentgenol 2014; (202):299-308
5. Radiology 2003; 229(1):261-268
6. Magn Reson Imaging 2018; 26(2):259-263
7. Asian J of Pharma Sci 2017; 12:235-249
8. U.S. patent Application Publication US 2018/0333109-A1
9. MCNP6.2 Release Notes 2018; LA-UR-18-20808
10. PLOS One 2014; 9(6):e99683
11. ESTAR, Physical Measurement Laboratory, National Institute of Standards & Technology.

What is claimed is:

1. An apparatus for X-ray mammography, comprising an X-ray tube, wherein:
    the X-ray tube comprises an anode and a focal spot track;
    the focal spot track comprises a tellurium foil and a cerium foil; and
    the tellurium foil and the cerium foil are attached to the anode.

2. The apparatus of claim 1, wherein the anode is a rotating molybdenum alloy anode, and wherein the rotating frequency of the anode is from about 3,600 rpm to about 10,000 rpm.

3. The apparatus of claim 2, wherein the anode is configured to emit an X-Ray beam, and wherein the angle between a rotation axis of the anode and a central axis of the X-Ray beam is about 6°.

4. The apparatus of claim 1, wherein:
    the tellurium foil is in a shape of 180° semicircular annular strip;
    the cerium foil is in a shape of 180° semicircular annular strip;
    the tellurium foil and the cerium foil are oriented with respect to each other to form a circle.

5. The apparatus of claim 4, wherein the radius of each of the 180° semicircular annular strips is from about 10 mm to about 100 mm.

6. The apparatus of claim 5, wherein the radius of each of the 180° semicircular annular strips is about 50 mm.

7. The apparatus of claim 4, wherein the tellurium foil and the cerium foil is each independently from about 5 µm to about 50 µm thick.

8. The apparatus of claim 4, wherein the tellurium foil and the cerium foil is each about 20 µm thick.

9. The apparatus of claim 1, wherein:
    the apparatus further comprises a filament configured to emit an electron beam, and
    the width of the filament is about 0.3 mm.

10. A method of X-ray imaging of a tissue in a subject, comprising:
    administering to a subject an iodine-based contrast agent;
    positioning the subject in an apparatus of claim 1; and
    acquiring an image of the tissue of the subject.

11. The method of claim 10, wherein the tissue is breast tissue.

* * * * *